(12) United States Patent
Godowski et al.

(10) Patent No.: US 6,368,853 B1
(45) Date of Patent: *Apr. 9, 2002

(54) TIE LIGAND HOMOLOGUES

(75) Inventors: Paul J. Godowski, Pacifica; Austin L. Gurney, Belmont, both of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/332,928

(22) Filed: Jun. 14, 1999

Related U.S. Application Data

(62) Division of application No. 08/933,821, filed on Sep. 19, 1997, now Pat. No. 5,972,338.

(51) Int. Cl.⁷ ............................ C12N 5/10; C12N 15/11; C12N 15/12; C07N 14/475
(52) U.S. Cl. ...................... 435/325; 536/23.1; 536/23.5; 530/350; 435/69.1; 435/320.1; 435/252.3; 435/254.11
(58) Field of Search ............................... 536/23.1, 23.5; 530/350; 435/69.1, 320.1, 325, 254.3, 254.11

(56) References Cited

U.S. PATENT DOCUMENTS

| | | |
|---|---|---|
| 5,447,860 A | 9/1995 | Ziegler |
| 5,521,073 A | 5/1996 | Davis et al. |
| 5,643,755 A | 7/1997 | Davis et al. |
| 5,650,490 A | 7/1997 | Davis et al. |

FOREIGN PATENT DOCUMENTS

| | | | |
|---|---|---|---|
| WO | WO 93/14124 | 7/1993 | |
| WO | WO 95/13387 | 5/1995 | |
| WO | WO 95/21866 | 8/1995 | |
| WO | WO 95/26364 | 10/1995 | |
| WO | WO 96/09381 | 3/1996 | |
| WO | WO 96/11269 | 4/1996 | |
| WO | WO 96/31598 | 10/1996 | |
| WO | WO 97/48804 | 12/1997 | |
| WO | WP 99/15653 | * 4/1999 | |

OTHER PUBLICATIONS

Davis et al., "Isolation of angiopoietin–1, a ligand for the TIE2 receptor, by secretion–trap expression cloning" *Cell* 87(7):1161–1169 (Dec. 27, 1996).

Dumont et al., "The endothelial–specific receptor tyrosine kinase, tek, is a member of a new subfamily of receptors" *Oncogene* 8(5):1293–1301 (May 1993).

Hanahan, D., "Signaling vascular morphogenesis and maintenance" *Science* 277:48–50 (1997).

Kaipainen et al., "Enhanced expression of the tie receptor tyrosine kinase messenger RNA in the vascular endothelium of metastatic melanomas" *Cancer Research* 54(24):6571–6577 (Dec. 15, 1994).

Korhonen et al., "Enhanced expression of the tie receptor tyrosine kinase in endothelial cells during neovascularization" *Blood* 80(10):2548–2555 (Nov. 15, 1992).

Maisonpierre et al., "Distinct rat genes with related profiles of expression define a TIE receptor tyrosine kinase family" *Oncogene* 8(6):1631–1637 (Jun. 1993).

Partanen et al., "Putative Tyrosine Kinases Expressed in K–562 Human Leukemia Cells" *Proc. Natl. Acad. Sci.* 87:8913–8917 (1990).

Suri et al., "Requisite role of angiopoietin–1, a ligand for the TIE2 receptor, during embryonic angiogenesis" *Cell* 87(7):1171–1180 (Dec. 27, 1996).

GenBank Accession Number T11442, CHR90008 Homo sapiens genomic clone 14C–1 5' and 3' similar to fibrogen–like domain, accessed Jan. 7, 1999 (Nov. 1993).

Kim et al., Molecular cloning, expression, and characterization of angiopoietin–related protein, J. Biol. Chem., 274(37):26523–26528, 1999.*

Procopio et al., Angiopoietin–1 and –2 coiled coil domains mediate distinct homo–oligoerization patterns, but fibrinogen–like domains mediate ligand activity, J. Biol. Chem., 274(42): 30196–30201, 1999.*

Maisonpierre et al., "Angiopoietin–2, a Natural Antagonists for Tie2 That Disrupts in vivo Angiogenesis" *Science*, 277:56–60 (Jul. 4, 1997).

* cited by examiner

Primary Examiner—Claire M. Kaufman
(74) Attorney, Agent, or Firm—Knobbe, Martens, Olson & Bear, LLP

(57) ABSTRACT

The present invention concerns isolated nucleic acid molecules encoding the novel TIE ligands NL1, NL5 and NL8, the proteins encoded by such nucleic acid molecules, as well as methods and means for making and using such nucleic acid and protein molecules.

14 Claims, 25 Drawing Sheets

```
GCGGACGCGT GGGTGAAATT GAAAATCAAG ATAAAAATGT TCACAATTAA 50
GCTCCTTCTT TTTATTGTTC CTCTAGTTAT TTCCTCCAGA ATTGATCAAG 100
ACAATTCATC ATTTGATTCT CTATCTCCAG AGCCAAAATC AAGATTTGCT 150
ATGTTAGACG ATGTAAAAAT TTTAGCCAAT GGCCTCCTTC AGTTGGGACA 200
TGGTCTTAAA GACTTTGTCC ATAAGACGAA GGGCCAAATT AATGACATAT 250
TTCAAAAACT CAACATATTT GATCAGTCTT TTTATGATCT ATCGCTGCAA 300
ACCAGTGAAA TCAAAGAAGA AGAAAAGGAA CTGAGAAGAA CTACATATAA 350
ACTACAAGTC AAAAATGAAG AGGTAAAGAA TATGTCACTT GAACTCAACT 400
CAAAACTTGA AAGCCTCCTA GAAGAAAAAA TTCTACTTCA ACAAAAAGTG 450
AAATATTTAG AAGAGCAACT AACTAACTTA ATTCAAAATC AACCTGAAAC 500
TCCAGAACAC CCAGAAGTAA CTTCACTTAA AACTTTTGTA GAAAAACAAG 550
ATAATAGCAT CAAAGACCTT CTCCAGACCG TGGAAGACCA ATATAAACAA 600
TTAAACCAAC AGCATAGTCA AATAAAAGAA ATAGAAAATC AGCTCAGAAG 650
GACTAGTATT CAAGAACCCA CAGAAATTTC TCTATCTTCC AAGCCAAGAG 700
CACCAAGAAC TACTCCCTTT CTTCAGTTGA ATGAAATAAG AAATGTAAAA 750
CATGATGGCA TTCCTGCTGA ATGTACCACC ATTTATAACA GAGGTGAACA 800
TACAAGTGGC ATGTATGCCA TCAGACCCAG CAACTCTCAA GTTTTTCATG 850
TCTACTGTGA TGTTATATCA GGTAGTCCAT GGACATTAAT TCAACATCGA 900
ATAGATGGAT CACAAAACTT CAATGAAACG TGGGAGAACT ACAAATATGG 950
TTTTGGGAGG CTTGATGGAG AATTTTGGTT GGGCCTAGAG AAGATATACT 1000
CCATAGTGAA GCAATCTAAT TATGTTTTAC GAATTGAGTT GGAAGACTGG 1050
AAAGACAACA AACATTATAT TGAATATTCT TTTTACTTGG GAAATCACGA 1100
AACCAACTAT ACGCTACATC TAGTTGCGAT TACTGGCAAT GTCCCCAATG 1150
CAATCCCGGA AAACAAAGAT TTGGTGTTTT CTACTTGGGA TCACAAAGCA 1200
AAAGGACACT TCAACTGTCC AGAGGGTTAT TCAGGAGGCT GGTGGTGGCA 1250
```

*Fig. 1A-1*

```
TGATGAGTGT GGAGAAAACA ACCTAAATGG TAAATATAAC AAACCAAGAG 1300
CAAAATCTAA GCCAGAGAGG AGAAGAGGAT TATCTTGGAA GTCTCAAAAT 1350
GGAAGGTTAT ACTCTATAAA ATCAACCAAA ATGTTGATCC ATCCAACAGA 1400
TTCAGAAAGC TTTGAATGAA CTGAGGCAAT TTAAAGGCAT ATTTAACCAT 1450
TAACTCATTC CAAGTTAATG TGGTCTAATA ATCTGGTATA AATCCTTAAG 1500
AGAAAGCTTG AGAAATAGAT TTTTTTTATC TTAAAGTCAC TGTCTATTTA 1550
AGATTAAACA TACAATCACA TAACCTTAAA GAATACCGTT TACATTTCTC 1600
AATCAAAATT CTTATAATAC TATTTGTTTT AAATTTTGTG ATGTGGGAAT 1650
CAATTTTAGA TGGTCACAAT CTAGATTATA ATCAATAGGT GAACTTATTA 1700
AATAACTTTT CTAAATAAAA AATTTAGAGA CTTTTATTTT AAAAGGCATC 1750
ATATGAGCTA ATATCACAAC TTTCCCAGTT TAAAAAACTA GTACTCTTGT 1800
TAAAACTCTA AACTTGACTA AATACAGAGG ACTGGTAATT GTACAGTTCT 1850
TAAATGTTGT AGTATTAATT TCAAAACTAA AAATCGTCAG CACAGAGTAT 1900
GTGTAAAAAT CTGTAATACA AATTTTTAAA CTGATGCTTC ATTTTGCTAC 1950
AAAATAATTT GGAGTAAATG TTTGATATGA TTTATTTATG AAACCTAATG 2000
AAGCAGAATT AAATACTGTA TTAAAATAAG TTCGCTGTCT TT 2042
```

*Fig. 1A-2*

```
Met Phe Thr Ile Lys Leu Leu Leu Phe Ile Val Pro Leu Val Ile
 1            5                  10                  15

Ser Ser Arg Ile Asp Gln Asp Asn Ser Ser Phe Asp Ser Leu Ser
             20                  25                  30

Pro Glu Pro Lys Ser Arg Phe Ala Met Leu Asp Asp Val Lys Ile
             35                  40                  45

Leu Ala Asn Gly Leu Leu Gln Leu Gly His Gly Leu Lys Asp Phe
             50                  55                  60

Val His Lys Thr Lys Gly Gln Ile Asn Asp Ile Phe Gln Lys Leu
             65                  70                  75

Asn Ile Phe Asp Gln Ser Phe Tyr Asp Leu Ser Leu Gln Thr Ser
             80                  85                  90

Glu Ile Lys Glu Glu Glu Lys Glu Leu Arg Arg Thr Thr Tyr Lys
             95                 100                 105

Leu Gln Val Lys Asn Glu Glu Val Lys Asn Met Ser Leu Glu Leu
            110                 115                 120

Asn Ser Lys Leu Glu Ser Leu Leu Glu Glu Lys Ile Leu Leu Gln
            125                 130                 135

Gln Lys Val Lys Tyr Leu Glu Glu Gln Leu Thr Asn Leu Ile Gln
            140                 145                 150

Asn Gln Pro Glu Thr Pro Glu His Pro Glu Val Thr Ser Leu Lys
            155                 160                 165

Thr Phe Val Glu Lys Gln Asp Asn Ser Ile Lys Asp Leu Leu Gln
            170                 175                 180

Thr Val Glu Asp Gln Tyr Lys Gln Leu Asn Gln Gln His Ser Gln
            185                 190                 195

Ile Lys Glu Ile Glu Asn Gln Leu Arg Arg Thr Ser Ile Gln Glu
            200                 205                 210

Pro Thr Glu Ile Ser Leu Ser Ser Lys Pro Arg Ala Pro Arg Thr
            215                 220                 225

Thr Pro Phe Leu Gln Leu Asn Glu Ile Arg Asn Val Lys His Asp
            230                 235                 240
```

*Fig. 1B-1*

```
Gly Ile Pro Ala Glu Cys Thr Thr Ile Tyr Asn Arg Gly Glu His
                245                 250                 255

Thr Ser Gly Met Tyr Ala Ile Arg Pro Ser Asn Ser Gln Val Phe
                260                 265                 270

His Val Tyr Cys Asp Val Ile Ser Gly Ser Pro Trp Thr Leu Ile
                275                 280                 285

Gln His Arg Ile Asp Gly Ser Gln Asn Phe Asn Glu Thr Trp Glu
                290                 295                 300

Asn Tyr Lys Tyr Gly Phe Gly Arg Leu Asp Gly Glu Phe Trp Leu
                305                 310                 315

Gly Leu Glu Lys Ile Tyr Ser Ile Val Lys Gln Ser Asn Tyr Val
                320                 325                 330

Leu Arg Ile Glu Leu Glu Asp Trp Lys Asp Asn Lys His Tyr Ile
                335                 340                 345

Glu Tyr Ser Phe Tyr Leu Gly Asn His Glu Thr Asn Tyr Thr Leu
                350                 355                 360

His Leu Val Ala Ile Thr Gly Asn Val Pro Asn Ala Ile Pro Glu
                365                 370                 375

Asn Lys Asp Leu Val Phe Ser Thr Trp Asp His Lys Ala Lys Gly
                380                 385                 390

His Phe Asn Cys Pro Glu Gly Tyr Ser Gly Gly Trp Trp Trp His
                395                 400                 405

Asp Glu Cys Gly Glu Asn Asn Leu Asn Gly Lys Tyr Asn Lys Pro
                410                 415                 420

Arg Ala Lys Ser Lys Pro Glu Arg Arg Gly Leu Ser Trp Lys
                425                 430                 435

Ser Gln Asn Gly Arg Leu Tyr Ser Ile Lys Ser Thr Lys Met Leu
                440                 445                 450

Ile His Pro Thr Asp Ser Glu Ser Phe Glu
                455                 460
```

*Fig. 1B-2*

```
GGCTGAGGGG AGGCCCGGAG CCTTTCTGGG GCCTGGGGGA TCCTCTTGCA  50
CTGGTGGGTG GAGAGAAGCG CCTGCAGCCA ACCAGGGTCA GGCTGTGCTC 100
ACAGTTTCCT CTGGCGGCAT GTAAAGGCTC ACAAAGGAG TTGGGAGTTC 150
AAATGAGGCT GCTGCGGACG GCCTGAGGAT GGACCCCAAG CCCTGGACCT 200
GCCGAGCGTG GCACTGAGGC AGCGGCTGAC GCTACTGTGA GGGAAGAAG 250
GTTGTGAGCA GCCCCGCAGG ACCCCTGGCC AGCCCTGGCC CCAGCCTCTG 300
CCGGAGCCCT CTGTGGAGGC AGAGCCAGTG GAGCCCAGTG AGGCAGGGCT 350
GCTTGGCAGC CACCGGCCTG CAACTCAGGA ACCCCTCCAG AGGCCATGGA 400
CAGGCTGCCC CGCTGACGGC CAGGGTGAAG CATGTGAGGA GCCGCCCCGG 450
AGCCAAGCAG GAGGGAAGAG GCTTTCATAG ATTCTATTCA CAAAGAATAA 500
CCACCATTTT GCAAGGACCA TGAGGCCACT GTGCGTGACA TGCTGGTGGC 550
TCGGACTGCT GGCTGCCATG GGAGCTGTTG CAGGCCAGGA GGACGGTTTT 600
GAGGGCACTG AGGAGGGCTC GCCAAGAGAG TTCATTTACC TAAACAGGTA 650
CAAGCGGGCG GGCGAGTCCC AGGACAAGTG CACCTACACC TTCATTGTGC 700
CCCAGCAGCG GGTCACGGGT GCCATCTGCG TCAACTCCAA GGAGCCTGAG 750
GTGCTTCTGG AGAACCGAGT GCATAAGCAG GAGCTAGAGC TGCTCAACAA 800
TGAGCTGCTC AAGCAGAAGC GGCAGATCGA GACGCTGCAG CAGCTGGTGG 850
AGGTGGACGG CGGCATTGTG AGCGAGGTGA AGCTGCTGCG CAAGGAGAGC 900
CGCAACATGA ACTCGCGGGT CACGCAGCTC TACATGCAGC TCCTGCACGA 950
GATCATCCGC AAGCGGGACA ACGCGTTGGA GCTCTCCCAG CTGGAGAACA 1000
GGATCCTGAA CCAGACAGCC GACATGCTGC AGCTGGCCAG CAAGTACAAG 1050
GACCTGGAGC ACAAGTACCA GCACCTGGCC ACACTGGCCC ACAACCAATC 1100
AGAGATCATC GCGCAGCTTG AGGAGCACTG CCAGAGGGTG CCCTCGGCCA 1150
GGCCCGTCCC CCAGCCACCC CCGCTGCCC CGCCCCGGGT CTACCAACCA 1200
```

Fig. 2A

```
CCCACCTACA ACCGCATCAT CAACCAGATC TCTACCAACG AGATCCAGAG 1250

TGACCAGAAC CTGAAGGTGC TGCCACCCCC TCTGCCCACT ATGCCCACTC 1300

TCACCAGCCT CCCATCTTCC ACCGACAAGC CGTCGGGCCC ATGGAGAGAC 1350

TGCCTGCAGG CCCTGGAGGA TGGCCACGAC ACCAGCTCCA TCTACCTGGT 1400

GAAGCCGGAG AACACCAACC GCCTCATGCA GGTGTGGTGC GACCAGAGAC 1450

ACGACCCCGG GGGCTGGACC GTCATCCAGA GACGCCTGGA TGGCTCTGTT 1500

AACTTCTTCA GGAACTGGGA GACGTACAAG CAAGGGTTTG GAACATTGA 1550

CGGCGAATAC TGGCTGGGCC TGGAGAACAT TTACTGGCTG ACGAACCAAG 1600

GCAACTACAA ACTCCTGGTG ACCATGGAGG ACTGGTCCGG CCGCAAAGTC 1650

TTTGCAGAAT ACGCCAGTTT CCGCCTGGAA CCTGAGAGCG AGTATTATAA 1700

GCTGCGGCTG GGGCGCTACC ATGGCAATGC GGGTGACTCC TTTACATGGC 1750

ACAACGGCAA GCAGTTCACC ACCCTGGACA GAGATCATGA TGTCTACACA 1800

GGAAACTGTG CCCACTACCA GAAGGGAGGC TGGTGGTATA ACGCCTGTGC 1850

CCACTCCAAC CTCAACGGGG TCTGGTACCG CGGGGGCCAT TACCGGAGCC 1900

GCTACCAGGA CGGAGTCTAC TGGGCTGAGT TCCGAGGAGG CTCTTACTCA 1950

CTCAAGAAAG TGGTGATGAT GATCCGACCG AACCCCAACA CCTTCCACTA 2000

AGCCAGCTCC CCCTCCTGAC CTCTCGTGGC CATTGCCAGG AGCCCACCCT 2050

GGTCACGCTG GCCACAGCAC AAAGAACAAC TCCTCACCAG TTCATCCTGA 2100

GGCTGGGAGG ACCGGGATGC TGGATTCTGT TTTCCGAAGT CACTGCAGCG 2150

GATGATGGAA CTGAATCGAT ACGGTGTTTT CTGTCCCTCC TACTTTCCTT 2200

CACACCAGAC AGCCCCTCAT GTCTCCAGGA CAGGACAGGA CTACAGACAA 2250

CTCTTTCTTT AAATAAATTA AGTCTCTACA ATAAAAAAAA 2290
```

*Fig. 2B*

| | | | | | | | | | | | | | | |
|---|---|---|---|---|---|---|---|---|---|---|---|---|---|---|
|Met|Arg|Pro|Leu|Cys|Val|Thr|Cys|Trp|Trp|Leu|Gly|Leu|Leu|Ala|
|1| | | |5| | | | |10| | | | |15|
|Ala|Met|Gly|Ala|Val|Ala|Gly|Gln|Glu|Asp|Gly|Phe|Glu|Gly|Thr|
| | | | |20| | | | |25| | | | |30|
|Glu|Glu|Gly|Ser|Pro|Arg|Glu|Phe|Ile|Tyr|Leu|Asn|Arg|Tyr|Lys|
| | | | |35| | | | |40| | | | |45|
|Arg|Ala|Gly|Glu|Ser|Gln|Asp|Lys|Cys|Thr|Tyr|Thr|Phe|Ile|Val|
| | | | |50| | | | |55| | | | |60|
|Pro|Gln|Gln|Arg|Val|Thr|Gly|Ala|Ile|Cys|Val|Asn|Ser|Lys|Glu|
| | | | |65| | | | |70| | | | |75|
|Pro|Glu|Val|Leu|Leu|Glu|Asn|Arg|Val|His|Lys|Gln|Glu|Leu|Glu|
| | | | |80| | | | |85| | | | |90|
|Leu|Leu|Asn|Asn|Glu|Leu|Leu|Lys|Gln|Lys|Arg|Gln|Ile|Glu|Thr|
| | | | |95| | | | |100| | | | |105|
|Leu|Gln|Gln|Leu|Val|Glu|Val|Asp|Gly|Gly|Ile|Val|Ser|Glu|Val|
| | | | |110| | | | |115| | | | |120|
|Lys|Leu|Leu|Arg|Lys|Glu|Ser|Arg|Asn|Met|Asn|Ser|Arg|Val|Thr|
| | | | |125| | | | |130| | | | |135|
|Gln|Leu|Tyr|Met|Gln|Leu|Leu|His|Glu|Ile|Ile|Arg|Lys|Arg|Asp|
| | | | |140| | | | |145| | | | |150|
|Asn|Ala|Leu|Glu|Leu|Ser|Gln|Leu|Glu|Asn|Arg|Ile|Leu|Asn|Gln|
| | | | |155| | | | |160| | | | |165|
|Thr|Ala|Asp|Met|Leu|Gln|Leu|Ala|Ser|Lys|Tyr|Lys|Asp|Leu|Glu|
| | | | |170| | | | |175| | | | |180|
|His|Lys|Tyr|Gln|His|Leu|Ala|Thr|Leu|Ala|His|Asn|Gln|Ser|Glu|
| | | | |185| | | | |190| | | | |195|
|Ile|Ile|Ala|Gln|Leu|Glu|Glu|His|Cys|Gln|Arg|Val|Pro|Ser|Ala|
| | | | |200| | | | |205| | | | |210|
|Arg|Pro|Val|Pro|Gln|Pro|Pro|Pro|Ala|Ala|Pro|Pro|Arg|Val|Tyr|
| | | | |215| | | | |220| | | | |225|
|Gln|Pro|Pro|Thr|Tyr|Asn|Arg|Ile|Ile|Asn|Gln|Ile|Ser|Thr|Asn|
| | | | |230| | | | |235| | | | |240|
|Glu|Ile|Gln|Ser|Asp|Gln|Asn|Leu|Lys|Val|Leu|Pro|Pro|Pro|Leu|
| | | | |245| | | | |250| | | | |255|

*Fig. 3A*

```
Pro Thr Met Pro Thr Leu Thr Ser Leu Pro Ser Ser Thr Asp Lys
                 260             265             270
Pro Ser Gly Pro Trp Arg Asp Cys Leu Gln Ala Leu Glu Asp Gly
                 275             280             285
His Asp Thr Ser Ser Ile Tyr Leu Val Lys Pro Glu Asn Thr Asn
                 290             295             300
Arg Leu Met Gln Val Trp Cys Asp Gln Arg His Asp Pro Gly Gly
                 305             310             315
Trp Thr Val Ile Gln Arg Leu Asp Gly Ser Val Asn Phe Phe
                 320             325             330
Arg Asn Trp Glu Thr Tyr Lys Gln Gly Phe Gly Asn Ile Asp Gly
                 335             340             345
Glu Tyr Trp Leu Gly Leu Glu Asn Ile Tyr Trp Leu Thr Asn Gln
                 350             355             360
Gly Asn Tyr Lys Leu Leu Val Thr Met Glu Asp Trp Ser Gly Arg
                 365             370             375
Lys Val Phe Ala Glu Tyr Ala Ser Phe Arg Leu Glu Pro Glu Ser
                 380             385             390
Glu Tyr Tyr Lys Leu Arg Leu Gly Arg Tyr His Gly Asn Ala Gly
                 395             400             405
Asp Ser Phe Thr Trp His Asn Gly Lys Gln Phe Thr Thr Leu Asp
                 410             415             420
Arg Asp His Asp Val Tyr Thr Gly Asn Cys Ala His Tyr Gln Lys
                 425             430             435
Gly Gly Trp Trp Tyr Asn Ala Cys Ala His Ser Asn Leu Asn Gly
                 440             445             450
Val Trp Tyr Arg Gly Gly His Tyr Arg Ser Arg Tyr Gln Asp Gly
                 455             460             465
Val Tyr Trp Ala Glu Phe Arg Gly Gly Ser Tyr Ser Leu Lys Lys
                 470             475             480
Val Val Met Met Ile Arg Pro Asn Pro Asn Thr Phe His
                 485             490         493
```

*Fig. 3B*

```
GCAGCTGGTT ACTGCATTTC TCCATGTGGC AGACAGAGCA AAGCCACAAC 50
GCTTTCTCTG CTGGATTAAA GACGGCCCAC AGACCAGAAC TTCCACTATA 100
CTACTTAAAA TTACATAGGT GGCTTGTCAA ATTCAATTGA TTAGTATTGT 150
AAAAGGAAAA AGAAGTTCCT TCTTACAGCT TGGATTCAAC GGTCCAAAAC 200
AAAAATGCAG CTGCCATTAA AGTCTCAGAT GAACAAACTT CTACACTGAT 250
TTTTAAAATC AAGAATAAGG GCAGCAAGTT TCTGGATTCA CTGAATCAAC 300
AGACACAAAA AGCTGGCAAT ATAGCAACTA TGAAGAGAAA AGCTACTAAT 350
AAAATTAACC CAACGCATAG AAGACTTTTT TTTCTCTTCT AAAAACAACT 400
AAGTAAAGAC TTAAATTTAA ACACATCATT TTACAACCTC ATTTCAAAAT 450
GAAGACTTTT ACCTGGACCC TAGGTGTGCT ATTCTTCCTA CTAGTGGACA 500
CTGGACATTG CAGAGGTGGA CAATTCAAAA TTAAAAAAAT AAACCAGAGA 550
AGATACCCTC GTGCCACAGA TGGTAAAGAG GAAGCAAAGA AATGTGCATA 600
CACATTCCTG GTACCTGAAC AAAGAATAAC AGGGCCAATC TGTGTCAACA 650
CCAAGGGGCA AGATGCAAGT ACCATTAAAG ACATGATCAC CAGGATGGAC 700
CTTGAAAACC TGAAGGATGT GCTCTCCAGG CAGAAGCGGG AGATAGATGT 750
TCTGCAACTG GTGGTGGATG TAGATGGAAA CATTGTGAAT GAGGTAAAGC 800
TGCTGAGAAA GGAAAGCCGT AACATGAACT CTCGTGTTAC TCAACTCTAT 850
ATGCAATTAT TACATGAGAT TATCCGTAAG AGGGATAATT CACTTGAACT 900
TTCCCAACTG GAAAACAAAA TCCTCAATGT CACCACAGAA ATGTTGAAGA 950
TGGCAACAAG ATACAGGGAA CTAGAGGTGA AATACGCTTC CTTGACTGAT 1000
CTTGTCAATA ACCAATCTGT GATGATCACT TTGTTGGAAG AACAGTGCTT 1050
GAGGATATTT TCCCGACAAG ACACCCATGT GTCTCCCCCA CTTGTCCAGG 1100
TGGTGCCACA ACATATTCCT AACAGCCAAC AGTATACTCC TGGTCTGCTG 1150
GGAGGTAACG AGATTCAGAG GGATCCAGGT TATCCCAGAG ATTTAATGCC 1200
```

*Fig. 4A*

```
ACCACCTGAT CTGGCAACTT CTCCCACCAA AAGCCCTTTC AAGATACCAC 1250
CGGTAACTTT CATCAATGAA GGACCATTCA AAGACTGTCA GCAAGCAAAA 1300
GAAGCTGGGC ATTCGGTCAG TGGGATTTAT ATGATTAAAC CTGAAAACAG 1350
CAATGGACCA ATGCAGTTAT GGTGTGAAAA CAGTTTGGAC CCTGGGGGTT 1400
GGACTGTTAT TCAGAAAAGA ACAGACGGCT CTGTCAACTT CTTCAGAAAT 1450
TGGGAAAATT ATAAGAAAGG GTTTGGAAAC ATTGACGGAG AATACTGGCT 1500
TGGACTGGAA AATATCTATA TGCTTAGCAA TCAAGATAAT TACAAGTTAT 1550
TGATTGAATT AGAAGACTGG AGTGATAAAA AGTCTATGC AGAATACAGC 1600
AGCTTTCGTC TGGAACCTGA AAGTGAATTC TATAGACTGC GCCTGGGAAC 1650
TTACCAGGGA AATGCAGGGG ATTCTATGAT GTGGCATAAT GGTAAACAAT 1700
TCACCACACT GGACAGAGAT AAAGATATGT ATGCAGGAAA CTGCGCCCAC 1750
TTTCATAAAG GAGGCTGGTG GTACAATGCC TGTGCACATT CTAACCTAAA 1800
TGGAGTATGG TACAGAGGAG GCCATTACAG AAGCAAGCAC CAAGATGGAA 1850
TTTTCTGGGC CGAATACAGA GGCGGGTCAT ACTCCTTAAG AGCAGTTCAG 1900
ATGATGATCA AGCCTATTGA CTGAAGAGAG ACACTCGCCA ATTTAAATGA 1950
CACAGAACTT TGTACTTTTC AGCTCTTAAA AATGTAAATG TTACATGTAT 2000
ATTACTTGGC ACAATTTATT TCTACACAGA AAGTTTTTAA AATGAATTTT 2050
ACCGTAACTA TAAAAGGGAA CCTATAAATG TAGTTTCATC TGTCGTCAAT 2100
TACTGCAGAA AATTATGTGT ATCCACAACC TAGTTATTTT AAAAATTATG 2150
TTGACTAAAT ACAAGTTTG TTTTCTAAAA TGTAAATATT TGCCACAATG 2200
TAAAGCAAAT CTTAGCTATA TTTTAAATCA TAAATAACAT GTTCAAGATA 2250
CTTAACAATT TATTTAAAAT CTAAGATTGC TCTAACGTCT AGTGAAAAAA 2300
ATATTTTTTA AATTTCAGCC AAATAATGCA TTTTATTTTA TAAAAATACA 2350
GACAGAAAAT TAGGGAGAAA CTTCTAGTTT TGCCAATAGA AAATGTTCTT 2400
```

*Fig. 4B*

```
CCATTGAATA AAAGTTATTT CAAATTGAAT TTGTGCCTTT CACACGTAAT 2450
GATTAAATCT GAATTCTTAA TAATATATCC TATGCTGATT TTCCCAAAAC 2500
ATGACCCATA GTATTAAATA CATATCATTT TTAAAAATAA AAAAAAACCC 2550
AAAAATAATG CATGCATAAT TTAAATGGTC AATTTATAAA GACAAATCTA 2600
TGAATGAATT TTTCAGTGTT ATCTTCATAT GATATGCTGA ACACCAAAAT 2650
CTCCAGAAAT GCATTTTATG TAGTTCTAAA ATCAGCAAAA TATTGGTATT 2700
ACAAAAATGC AGAATATTTA GTGTGCTACA GATCTGAATT ATAGTTCTAA 2750
TTTATTATTA CTTTTTTTCT AATTTACTGA TCTTACTACT ACAAAGAAAA 2800
AAAAACCCAA CCCATCTGCA ATTCAAATCA GAAAGTTTGG ACAGCTTTAC 2850
AAGTATTAGT GCATGCTCAG AACAGGTGGG ACTAAAACAA ACTCAAGGAA 2900
CTGTTGGCTG TTTTCCCGAT ACTGAGAATT CAACAGCTCC AGAGCAGAAG 2950
CCACAGGGGC ATAGCTTAGT CCAAACTGCT AATTTCATTT TACAGTGTAT 3000
GTAACGCTTA GTCTCACAGT GTCTTTAACT CATCTTTGCA ATCAACAACT 3050
TTACTAGTGA CTTTCTGGAA CAATTTCCTT TCAGGAATAC ATATTCACTG 3100
CTTAGAGGTG ACCTTGCCTT AATATATTTG TGAAGTTAAA ATTTTAAAGA 3150
TAGCTCATGA AACTTTTGCT TAAGCAAAAA GAAAACCTCG AATTGAAATG 3200
TGTGAGGCAA ACTATGCATG GAATAGCTT AATGTGAAGA TAATCATTTG 3250
GACAACTCAA ATCCATCAAC ATGACCAATG TTTTTCATCT GCCACATCTC 3300
AAAATAAAAC TTCTGGTGAA ACAAATTAAA CAAAATATCC AAACCTCAAA 3350
AAAAA 3355
```

*Fig. 4C*

```
Met Lys Thr Phe Thr Trp Thr Leu Gly Val Leu Phe Phe Leu Leu
 1               5                  10                  15

Val Asp Thr Gly His Cys Arg Gly Gly Gln Phe Lys Ile Lys Lys
                20                  25                  30

Ile Asn Gln Arg Arg Tyr Pro Arg Ala Thr Asp Gly Lys Glu Glu
                35                  40                  45

Ala Lys Lys Cys Ala Tyr Thr Phe Leu Val Pro Glu Gln Arg Ile
                50                  55                  60

Thr Gly Pro Ile Cys Val Asn Thr Lys Gly Gln Asp Ala Ser Thr
                65                  70                  75

Ile Lys Asp Met Ile Thr Arg Met Asp Leu Glu Asn Leu Lys Asp
                80                  85                  90

Val Leu Ser Arg Gln Lys Arg Glu Ile Asp Val Leu Gln Leu Val
                95                 100                 105

Val Asp Val Asp Gly Asn Ile Val Asn Glu Val Lys Leu Leu Arg
               110                 115                 120

Lys Glu Ser Arg Asn Met Asn Ser Arg Val Thr Gln Leu Tyr Met
               125                 130                 135

Gln Leu Leu His Glu Ile Ile Arg Lys Arg Asp Asn Ser Leu Glu
               140                 145                 150

Leu Ser Gln Leu Glu Asn Lys Ile Leu Asn Val Thr Thr Glu Met
               155                 160                 165

Leu Lys Met Ala Thr Arg Tyr Arg Glu Leu Glu Val Lys Tyr Ala
               170                 175                 180

Ser Leu Thr Asp Leu Val Asn Asn Gln Ser Val Met Ile Thr Leu
               185                 190                 195

Leu Glu Glu Gln Cys Leu Arg Ile Phe Ser Arg Gln Asp Thr His
               200                 205                 210

Val Ser Pro Pro Leu Val Gln Val Val Pro Gln His Ile Pro Asn
               215                 220                 225

Ser Gln Gln Tyr Thr Pro Gly Leu Leu Gly Gly Asn Glu Ile Gln
               230                 235                 240

Arg Asp Pro Gly Tyr Pro Arg Asp Leu Met Pro Pro Pro Asp Leu
               245                 250                 255
```

*Fig. 5A*

```
Ala Thr Ser Pro Thr Lys Ser Pro Phe Lys Ile Pro Pro Val Thr
                260                 265                 270
Phe Ile Asn Glu Gly Pro Phe Lys Asp Cys Gln Gln Ala Lys Glu
                275                 280                 285
Ala Gly His Ser Val Ser Gly Ile Tyr Met Ile Lys Pro Glu Asn
                290                 295                 300
Ser Asn Gly Pro Met Gln Leu Trp Cys Glu Asn Ser Leu Asp Pro
                305                 310                 315
Gly Gly Trp Thr Val Ile Gln Lys Arg Thr Asp Gly Ser Val Asn
                320                 325                 330
Phe Phe Arg Asn Trp Glu Asn Tyr Lys Lys Gly Phe Gly Asn Ile
                335                 340                 345
Asp Gly Glu Tyr Trp Leu Gly Leu Glu Asn Ile Tyr Met Leu Ser
                350                 355                 360
Asn Gln Asp Asn Tyr Lys Leu Leu Ile Glu Leu Glu Asp Trp Ser
                365                 370                 375
Asp Lys Lys Val Tyr Ala Glu Tyr Ser Ser Phe Arg Leu Glu Pro
                380                 385                 390
Glu Ser Glu Phe Tyr Arg Leu Arg Leu Gly Thr Tyr Gln Gly Asn
                395                 400                 405
Ala Gly Asp Ser Met Met Trp His Asn Gly Lys Gln Phe Thr Thr
                410                 415                 420
Leu Asp Arg Asp Lys Asp Met Tyr Ala Gly Asn Cys Ala His Phe
                425                 430                 435
His Lys Gly Gly Trp Trp Tyr Asn Ala Cys Ala His Ser Asn Leu
                440                 445                 450
Asn Gly Val Trp Tyr Arg Gly Gly His Tyr Arg Ser Lys His Gln
                455                 460                 465
Asp Gly Ile Phe Trp Ala Glu Tyr Arg Gly Gly Ser Tyr Ser Leu
                470                 475                 480
Arg Ala Val Gln Met Met Ile Lys Pro Ile Asp
                485                 490 491
```

*Fig. 5B*

```
GGCTCAGAGG CCCCACTGGA CCCTCGGCTC TTCCTTGGAC TTCTTGTGTG  50
TTCTGTGAGC TTCGCTGGAT TCAGGGTCTT GGGCATCAGA GGTGAGAGGG 100
TGGGAAGGTC CGCCGCGATG GGGAAGCCCT GGCTGCGTGC GCTACAGCTG 150
CTGCTCCTGC TGGGCGCGTC GTGGGCGCGG GCGGGCGCCC CGCGCTGCAC 200
CTACACCTTC GTGCTGCCCC CGCAGAAGTT CACGGGCGCT GTGTGCTGGA 250
GCGGCCCCGC ATCCACGCGG GCGACGCCCG AGGCCGCCAA CGCCAGCGAG 300
CTGGCGGCGC TGCGCATGCG CGTCGGCCGC CACGAGGAGC TGTTACGCGA 350
GCTGCAGAGG CTGGCGGCGG CCGACGGCGC CGTGGCCGGC GAGGTGCGCG 400
CGCTGCGCAA GGAGAGCCGC GGCCTGAGCG CGCGCCTGGG CCAGTTGCGC 450
GCGCAGCTGC AGCACGAGGC GGGGCCCGGG GCGGGCCCGG GGCGGATCT 500
GGGGGCGGAG CCTGCCGCGG CGCTGGCGCT GCTCGGGGAG CGCGTGCTCA 550
ACGCGTCCGC CGAGGCTCAG CGCGCAGCCG CCCGGTTCCA CCAGCTGGAC 600
GTCAAGTTCC GCGAGCTGGC GCAGCTCGTC ACCCAGCAGA GCAGTCTCAT 650
CGCCCGCCTG GAGCGCCTGT GCCCGGGAGG CGCGGGCGGG CAGCAGCAGG 700
TCCTGCCGCC ACCCCACTG GTGCCTGTGG TTCCGGTCCG TCTTGTGGGT 750
AGCACCAGTG ACACCAGTAG GATGCTGGAC CCAGCCCCAG AGCCCCAGAG 800
AGACCAGACC CAGAGACAGC AGGAGCCCAT GGCTTCTCCC ATGCCTGCAG 850
GTCACCCTGC GGTCCCCACC AAGCCTGTGG GCCCGTGGCA GGATTGTGCA 900
GAGGCCCGCC AGGCAGGCCA TGAACAGAGT GGAGTGTATG AACTGCGAGT 950
GGGCCGTCAC GTAGTGTCAG TATGGTGTGA GCAGCAACTG GAGGGTGGAG 1000
GCTGGACTGT GATCCAGCGG AGGCAAGATG GTTCAGTCAA CTTCTTCACT 1050
ACCTGGCAGC ACTATAAGGC GGGCTTTGGG CGGCCAGACG GAGAATACTG 1100
GCTGGGCCTT GAACCCGTGT ATCAGCTGAC CAGCCGTGGG GACCATGAGC 1150
TGCTGGTTCT CCTGGAGGAC TGGGGGGGCC GTGGAGCACG TGCCCACTAT 1200
```

*Fig. 6A*

```
GATGGCTTCT CCCTGGAACC CGAGAGCGAC CACTACCGCC TGCGGCTTGG 1250

CCAGTACCAT GGTGATGCTG GAGACTCTCT TTCCTGGCAC AATGACAAGC 1300

CCTTCAGCAC CGTGGATAGG GACCGAGACT CCTATTCTGG TAACTGTGCC 1350

CTGTACCAGC GGGGAGGCTG GTGGTACCAT GCCTGTGCCC ACTCCAACCT 1400

CAACGGTGTG TGGCACCACG GCGGCCACTA CCGAAGCCGC TACCAGGATG 1450

GTGTCTACTG GGCTGAGTTT CGTGGTGGGG CATATTCTCT CAGGAAGGCC 1500

GCCATGCTCA TTCGGCCCCT GAAGCTGTGA CTCTGTGTTC CTCTGTCCCC 1550

TAGGCCCTAG AGGACATTGG TCAGCAGGAG CCCAAGTTGT TCTGGCCACA 1600

CCTTCTTTGT GGCTCAGTGC CAATGTGTCC CACAGAACTT CCCACTGTGG 1650

ATCTGTGACC CTGGGCGCTG AAAATGGGAC CCAGGAATCC CCCCGTCAA 1700

TATCTTGGCC TCAGATGGCT CCCCAAGGTC ATTCATATCT CGGTTTGAGC 1750

TCATATCTTA TAATAACACA AAGTAGCCAC 1780
```

*Fig. 6B*

Met Gly Lys Pro Trp Leu Arg Ala Leu Gln Leu Leu Leu Leu Leu
 1              5                   10                  15

Gly Ala Ser Trp Ala Arg Ala Gly Ala Pro Arg Cys Thr Tyr Thr
            20                  25                  30

Phe Val Leu Pro Pro Gln Lys Phe Thr Gly Ala Val Cys Trp Ser
            35                  40                  45

Gly Pro Ala Ser Thr Arg Ala Thr Pro Glu Ala Ala Asn Ala Ser
            50                  55                  60

Glu Leu Ala Ala Leu Arg Met Arg Val Gly Arg His Glu Glu Leu
            65                  70                  75

Leu Arg Glu Leu Gln Arg Leu Ala Ala Asp Gly Ala Val Ala
            80                  85                  90

Gly Glu Val Arg Ala Leu Arg Lys Glu Ser Arg Gly Leu Ser Ala
            95                  100                 105

Arg Leu Gly Gln Leu Arg Ala Gln Leu Gln His Glu Ala Gly Pro
            110                 115                 120

Gly Ala Gly Pro Gly Ala Asp Leu Gly Ala Glu Pro Ala Ala Ala
            125                 130                 135

Leu Ala Leu Leu Gly Glu Arg Val Leu Asn Ala Ser Ala Glu Ala
            140                 145                 150

Gln Arg Ala Ala Ala Arg Phe His Gln Leu Asp Val Lys Phe Arg
            155                 160                 165

Glu Leu Ala Gln Leu Val Thr Gln Gln Ser Ser Leu Ile Ala Arg
            170                 175                 180

Leu Glu Arg Leu Cys Pro Gly Gly Ala Gly Gly Gln Gln Gln Val
            185                 190                 195

Leu Pro Pro Pro Pro Leu Val Pro Val Val Pro Val Arg Leu Val
            200                 205                 210

Gly Ser Thr Ser Asp Thr Ser Arg Met Leu Asp Pro Ala Pro Glu
            215                 220                 225

Pro Gln Arg Asp Gln Thr Gln Arg Gln Gln Glu Pro Met Ala Ser
            230                 235                 240

Pro Met Pro Ala Gly His Pro Ala Val Pro Thr Lys Pro Val Gly
            245                 250                 255

*Fig. 7A*

```
Pro Trp Gln Asp Cys Ala Glu Ala Arg Gln Ala Gly His Glu Gln
            260                 265                 270

Ser Gly Val Tyr Glu Leu Arg Val Gly Arg His Val Val Ser Val
            275                 280                 285

Trp Cys Glu Gln Gln Leu Glu Gly Gly Gly Trp Thr Val Ile Gln
            290                 295                 300

Arg Arg Gln Asp Gly Ser Val Asn Phe Phe Thr Thr Trp Gln His
            305                 310                 315

Tyr Lys Ala Gly Phe Gly Arg Pro Asp Gly Glu Tyr Trp Leu Gly
            320                 325                 330

Leu Glu Pro Val Tyr Gln Leu Thr Ser Arg Gly Asp His Glu Leu
            335                 340                 345

Leu Val Leu Leu Glu Asp Trp Gly Gly Arg Gly Ala Arg Ala His
            350                 355                 360

Tyr Asp Gly Phe Ser Leu Glu Pro Glu Ser Asp His Tyr Arg Leu
            365                 370                 375

Arg Leu Gly Gln Tyr His Gly Asp Ala Gly Asp Ser Leu Ser Trp
            380                 385                 390

His Asn Asp Lys Pro Phe Ser Thr Val Asp Arg Asp Arg Asp Ser
            395                 400                 405

Tyr Ser Gly Asn Cys Ala Leu Tyr Gln Arg Gly Gly Trp Trp Tyr
            410                 415                 420

His Ala Cys Ala His Ser Asn Leu Asn Gly Val Trp His His Gly
            425                 430                 435

Gly His Tyr Arg Ser Arg Tyr Gln Asp Gly Val Tyr Trp Ala Glu
            440                 445                 450

Phe Arg Gly Gly Ala Tyr Ser Leu Arg Lys Ala Ala Met Leu Ile
            455                 460                 465

Arg Pro Leu Lys Leu
            470
```

*Fig. 7B*

DNA 22779 H&E

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
       (A) LENGTH: 2290 base pairs
       (B) TYPE: Nucleic Acid
       (C) STRANDEDNESS: Single
       (D) TOPOLOGY: Linear (xi) SEQUENCE DESCRIPTION: SEQ ID NO: 1:

| | |
|---|---:|
| GGCTGAGGGG AGGCCCGGAG CCTTTCTGGG GCCTGGGGGA TCCTCTTGCA | 50 |
| CTGGTGGGTG GAGAGAAGCG CCTGCAGCCA ACCAGGGTCA GGCTGTGCTC | 100 |
| ACAGTTTCCT CTGGCGGCAT GTAAAGGCTC CACAAAGGAG TTGGGAGTTC | 150 |
| AAATGAGGCT GCTGCGGACG GCCTGAGGAT GGACCCCAAG CCCTGGACCT | 200 |
| GCCGAGCGTG GCACTGAGGC AGCGGCTGAC GCTACTGTGA GGGAAAGAAG | 250 |
| GTTGTGAGCA GCCCCGCAGG ACCCCTGGCC AGCCCTGGCC CCAGCCTCTG | 300 |
| CCGGAGCCCT CTGTGGAGGC AGAGCCAGTG GAGCCCAGTG AGGCAGGGCT | 350 |
| GCTTGGCAGC CACCGGCCTG CAACTCAGGA ACCCCTCCAG AGGCCATGGA | 400 |
| CAGGCTGCCC CGCTGACGGC CAGGGTGAAG CATGTGAGGA GCCGCCCCGG | 450 |
| AGCCAAGCAG GAGGGAAGAG GCTTTCATAG ATTCTATTCA CAAAGAATAA | 500 |
| CCACCATTTT GCAAGGACCA TGAGGCCACT GTGCGTGACA TGCTGGTGGC | 550 |
| TCGGACTGCT GGCTGCCATG GGAGCTGTTG CAGGCCAGGA GGACGGTTTT | 600 |
| GAGGGCACTG AGGAGGGCTC GCCAAGAGAG TTCATTTACC TAAACAGGTA | 650 |
| CAAGCGGGCG GGCGAGTCCC AGGACAAGTG CACCTACACC TTCATTGTGC | 700 |
| CCCAGCAGCG GGTCACGGGT GCCATCTGCG TCAACTCCAA GGAGCCTGAG | 750 |
| GTGCTTCTGG AGAACCGAGT GCATAAGCAG GAGCTAGAGC TGCTCAACAA | 800 |
| TGAGCTGCTC AAGCAGAAGC GGCAGATCGA ACGCTGCAG CAGCTGGTGG | 850 |
| AGGTGGACGG CGGCATTGTG AGCGAGGTGA AGCTGCTGCG CAAGGAGAGC | 900 |
| CGCAACATGA ACTCGCGGGT CACGCAGCTC TACATGCAGC TCCTGCACGA | 950 |
| GATCATCCGC AAGCGGGACA ACGCGTTGGA GCTCTCCCAG CTGGAGAACA | 1000 |
| GGATCCTGAA CCAGACAGCC GACATGCTGC AGCTGGCCAG CAAGTACAAG | 1050 |
| GACCTGGAGC ACAAGTACCA GCACCTGGCC ACACTGGCCC ACAACCAATC | 1100 |
| AGAGATCATC GCGCAGCTTG AGGAGCACTG CCAGAGGGTG CCCTCGGCCA | 1150 |
| GGCCCGTCCC CCAGCCACCC CCCGCTGCCC CGCCCCGGGT CTACCAACCA | 1200 |
| CCCACCTACA ACCGCATCAT CAACCAGATC TCTACCAACG AGATCCAGAG | 1250 |
| TGACCAGAAC CTGAAGGTGC TGCCACCCCC TCTGCCCACT ATGCCCACTC | 1300 |
| TCACCAGCCT CCCATCTTCC ACCGACAAGC CGTCGGGCCC ATGGAGAGAC | 1350 |
| TGCCTGCAGG CCCTGGAGGA TGGCCACGAC ACCAGCTCCA TCTACCTGGT | 1400 |
| GAAGCCGGAG AACACCAACC GCCTCATGCA GGTGTGGTGC GACCAGAGAC | 1450 |
| ACGACCCCGG GGGCTGGACC GTCATCCAGA GACGCCTGGA TGGCTCTGTT | 1500 |
| AACTTCTTCA GGAACTGGGA GACGTACAAG CAAGGGTTTG GAACATTGA | 1550 |

```
CGGCGAATAC TGGCTGGGCC TGGAGAACAT TTACTGGCTG ACGAACCAAG          1600

GCAACTACAA ACTCCTGGTG ACCATGGAGG ACTGGTCCGG CCGCAAAGTC          1650

TTTGCAGAAT ACGCCAGTTT CCGCCTGGAA CCTGAGAGCG AGTATTATAA          1700

GCTGCGGCTG GGGCGCTACC ATGGCAATGC GGGTGACTCC TTTACATGGC          1750

ACAACGGCAA GCAGTTCACC ACCCTGGACA GAGATCATGA TGTCTACACA          1800

GGAAACTGTG CCCACTACCA GAAGGGAGGC TGGTGGTATA ACGCCTGTGC          1850

CCACTCCAAC CTCAACGGGG TCTGGTACCG CGGGGGCCAT TACCGGAGCC          1900

GCTACCAGGA CGGAGTCTAC TGGGCTGAGT TCCGAGGAGG CTCTTACTCA          1950

CTCAAGAAAG TGGTGATGAT GATCCGACCG AACCCCAACA CCTTCCACTA          2000

AGCCAGCTCC CCCTCCTGAC CTCTCGTGGC CATTGCCAGG AGCCCACCCT          2050

GGTCACGCTG CCACAGCAC AAAGAACAAC TCCTCACCAG TTCATCCTGA           2100

GGCTGGGAGG ACCGGGATGC TGGATTCTGT TTTCCGAAGT CACTGCAGCG          2150

GATGATGGAA CTGAATCGAT ACGGTGTTTT CTGTCCCTCC TACTTTCCTT          2200

CACACCAGAC AGCCCCTCAT GTCTCCAGGA CAGGACAGGA CTACAGACAA          2250

CTCTTTCTTT AAATAAATTA AGTCTCTACA ATAAAAAAAA                     2290

(2) INFORMATION FOR SEQ ID NO: 2:

(i) SEQUENCE CHARACTERISTICS:
        (A) LENGTH: 493 amino acids
        (B) TYPE: Amino Acid
        (D) TOPOLOGY: Linear (xi) SEQUENCE DESCRIPTION: SEQ ID NO: 2:

Met Arg Pro Leu Cys Val Thr Cys Trp Trp Leu Gly Leu Leu Ala
 1               5                  10                  15

Ala Met Gly Ala Val Ala Gly Gln Glu Asp Gly Phe Glu Gly Thr
                20                  25                  30

Glu Glu Gly Ser Pro Arg Glu Phe Ile Tyr Leu Asn Arg Tyr Lys
                35                  40                  45

Arg Ala Gly Glu Ser Gln Asp Lys Cys Thr Tyr Thr Phe Ile Val
                50                  55                  60

Pro Gln Gln Arg Val Thr Gly Ala Ile Cys Val Asn Ser Lys Glu
                65                  70                  75

Pro Glu Val Leu Leu Glu Asn Arg Val His Lys Gln Glu Leu Glu
                80                  85                  90

Leu Leu Asn Asn Glu Leu Leu Lys Gln Lys Arg Gln Ile Glu Thr
                95                  100                 105

Leu Gln Gln Leu Val Glu Val Asp Gly Gly Ile Val Ser Glu Val
                110                 115                 120

Lys Leu Leu Arg Lys Glu Ser Arg Asn Met Asn Ser Arg Val Thr
                125                 130                 135

Gln Leu Tyr Met Gln Leu Leu His Glu Ile Ile Arg Lys Arg Asp
                140                 145                 150

Asn Ala Leu Glu Leu Ser Gln Leu Glu Asn Arg Ile Leu Asn Gln
                155                 160                 165

Thr Ala Asp Met Leu Gln Leu Ala Ser Lys Tyr Lys Asp Leu Glu
                170                 175                 180

His Lys Tyr Gln His Leu Ala Thr Leu Ala His Asn Gln Ser Glu
                185                 190                 195
```

-continued

```
Ile Ile Ala Gln Leu Glu Glu His Cys Gln Arg Val Pro Ser Ala
            200                 205                 210
Arg Pro Val Pro Gln Pro Pro Ala Ala Pro Pro Arg Val Tyr
            215                 220                 225
Gln Pro Pro Thr Tyr Asn Arg Ile Ile Asn Gln Ile Ser Thr Asn
            230                 235                 240
Glu Ile Gln Ser Asp Gln Asn Leu Lys Val Leu Pro Pro Pro Leu
            245                 250                 255
Pro Thr Met Pro Thr Leu Thr Ser Leu Pro Ser Ser Thr Asp Lys
            260                 265                 270
Pro Ser Gly Pro Trp Arg Asp Cys Leu Gln Ala Leu Glu Asp Gly
            275                 280                 285
His Asp Thr Ser Ser Ile Tyr Leu Val Lys Pro Glu Asn Thr Asn
            290                 295                 300
Arg Leu Met Gln Val Trp Cys Asp Gln Arg His Asp Pro Gly Gly
            305                 310                 315
Trp Thr Val Ile Gln Arg Arg Leu Asp Gly Ser Val Asn Phe Phe
            320                 325                 330
Arg Asn Trp Glu Thr Tyr Lys Gln Gly Phe Gly Asn Ile Asp Gly
            335                 340                 345
Glu Tyr Trp Leu Gly Leu Glu Asn Ile Tyr Trp Leu Thr Asn Gln
            350                 355                 360
Gly Asn Tyr Lys Leu Leu Val Thr Met Glu Asp Trp Ser Gly Arg
            365                 370                 375
Lys Val Phe Ala Glu Tyr Ala Ser Phe Arg Leu Glu Pro Glu Ser
            380                 385                 390
Glu Tyr Tyr Lys Leu Arg Leu Gly Arg Tyr His Gly Asn Ala Gly
            395                 400                 405
Asp Ser Phe Thr Trp His Asn Gly Lys Gln Phe Thr Thr Leu Asp
            410                 415                 420
Arg Asp His Asp Val Tyr Thr Gly Asn Cys Ala His Tyr Gln Lys
            425                 430                 435
Gly Gly Trp Trp Tyr Asn Ala Cys Ala His Ser Asn Leu Asn Gly
            440                 445                 450
Val Trp Tyr Arg Gly Gly His Tyr Arg Ser Arg Tyr Gln Asp Gly
            455                 460                 465
Val Tyr Trp Ala Glu Phe Arg Gly Gly Ser Tyr Ser Leu Lys Lys
            470                 475                 480
Val Val Met Met Ile Arg Pro Asn Pro Asn Thr Phe His
            485                 490         493
```

(2) INFORMATION FOR SEQ ID NO: 3:

(i) SEQUENCE CHARACTERISTICS:
        (A) LENGTH: 3355 base pairs
        (B) TYPE: Nucleic Acid
        (C) STRANDEDNESS: Single
        (D) TOPOLOGY: Linear (xi) SEQUENCE DESCRIPTION: SEQ ID NO: 3:

```
GCAGCTGGTT ACTGCATTTC TCCATGTGGC AGACAGAGCA AAGCCACAAC              50

GCTTTCTCTG CTGGATTAAA GACGGCCCAC AGACCAGAAC TTCCACTATA             100

CTACTTAAAA TTACATAGGT GGCTTGTCAA ATTCAATTGA TTAGTATTGT             150

AAAAGGAAAA AGAAGTTCCT TCTTACAGCT TGGATTCAAC GGTCCAAAAC             200
```

```
AAAAATGCAG CTGCCATTAA AGTCTCAGAT GAACAAACTT CTACACTGAT           250

TTTTAAAATC AAGAATAAGG GCAGCAAGTT TCTGGATTCA CTGAATCAAC           300

AGACACAAAA AGCTGGCAAT ATAGCAACTA TGAAGAGAAA AGCTACTAAT           350

AAAATTAACC CAACGCATAG AAGACTTTTT TTTCTCTTCT AAAAACAACT           400

AAGTAAAGAC TTAAATTTAA ACACATCATT TTACAACCTC ATTTCAAAAT           450

GAAGACTTTT ACCTGGACCC TAGGTGTGCT ATTCTTCCTA CTAGTGGACA           500

CTGGACATTG CAGAGGTGGA CAATTCAAAA TTAAAAAAAT AAACCAGAGA           550

AGATACCCTC GTGCCACAGA TGGTAAAGAG GAAGCAAAGA AATGTGCATA           600

CACATTCCTG GTACCTGAAC AAAGAATAAC AGGGCCAATC TGTGTCAACA           650

CCAAGGGGCA AGATGCAAGT ACCATTAAAG ACATGATCAC CAGGATGGAC           700

CTTGAAAACC TGAAGGATGT GCTCTCCAGG CAGAAGCGGG AGATAGATGT           750

TCTGCAACTG GTGGTGGATG TAGATGGAAA CATTGTGAAT GAGGTAAAGC           800

TGCTGAGAAA GGAAAGCCGT AACATGAACT CTCGTGTTAC TCAACTCTAT           850

ATGCAATTAT TACATGAGAT TATCCGTAAG AGGGATAATT CACTTGAACT           900

TTCCCAACTG GAAAACAAAA TCCTCAATGT CACCACAGAA ATGTTGAAGA           950

TGGCAACAAG ATACAGGGAA CTAGAGGTGA ATACGCTTC CTTGACTGAT           1000

CTTGTCAATA ACCAATCTGT GATGATCACT TTGTTGGAAG AACAGTGCTT           1050

GAGGATATTT TCCCGACAAG ACACCCATGT GTCTCCCCCA CTTGTCCAGG           1100

TGGTGCCACA ACATATTCCT AACAGCCAAC AGTATACTCC TGGTCTGCTG           1150

GGAGGTAACG AGATTCAGAG GGATCCAGGT TATCCCAGAG ATTTAATGCC           1200

ACCACCTGAT CTGGCAACTT CTCCCACCAA AAGCCCTTTC AAGATACCAC           1250

CGGTAACTTT CATCAATGAA GGACCATTCA AAGACTGTCA GCAAGCAAAA           1300

GAAGCTGGGC ATTCGGTCAG TGGGATTTAT ATGATTAAAC CTGAAAACAG           1350

CAATGGACCA ATGCAGTTAT GGTGTGAAAA CAGTTTGGAC CCTGGGGGTT           1400

GGACTGTTAT TCAGAAAAGA ACAGACGGCT CTGTCAACTT CTTCAGAAAT           1450

TGGGAAAATT ATAAGAAAGG GTTTGGAAAC ATTGACGGAG AATACTGGCT           1500

TGGACTGGAA AATATCTATA TGCTTAGCAA TCAAGATAAT TACAAGTTAT           1550

TGATTGAATT AGAAGACTGG AGTGATAAAA AAGTCTATGC AGAATACAGC           1600

AGCTTTCGTC TGGAACCTGA AAGTGAATTC TATAGACTGC GCCTGGGAAC           1650

TTACCAGGGA AATGCAGGGG ATTCTATGAT GTGGCATAAT GGTAAACAAT           1700

TCACCACACT GGACAGAGAT AAAGATATGT ATGCAGGAAA CTGCGCCCAC           1750

TTTCATAAAG GAGGCTGGTG GTACAATGCC TGTGCACATT CTAACCTAAA           1800

TGGAGTATGG TACAGAGGAG GCCATTACAG AAGCAAGCAC CAAGATGGAA           1850

TTTTCTGGGC CGAATACAGA GGCGGGTCAT ACTCCTTAAG AGCAGTTCAG           1900

ATGATGATCA AGCCTATTGA CTGAAGAGAG ACACTCGCCA ATTTAAATGA           1950

CACAGAACTT TGTACTTTTC AGCTCTTAAA AATGTAAATG TTACATGTAT           2000

ATTACTTGGC ACAATTTATT TCTACACAGA AAGTTTTTAA AATGAATTTT           2050

ACCGTAACTA TAAAAGGGAA CCTATAAATG TAGTTTCATC TGTCGTCAAT           2100

TACTGCAGAA AATTATGTGT ATCCACAACC TAGTTATTTT AAAAATTATG           2150
```

```
TTGACTAAAT ACAAAGTTTG TTTTCTAAAA TGTAAATATT TGCCACAATG              2200

TAAAGCAAAT CTTAGCTATA TTTTAAATCA TAAATAACAT GTTCAAGATA              2250

CTTAACAATT TATTTAAAAT CTAAGATTGC TCTAACGTCT AGTGAAAAAA              2300

ATATTTTTTA AATTTCAGCC AAATAATGCA TTTTATTTTA TAAAAATACA              2350

GACAGAAAAT TAGGGAGAAA CTTCTAGTTT TGCCAATAGA AAATGTTCTT              2400

CCATTGAATA AAAGTTATTT CAAATTGAAT TTGTGCCTTT CACACGTAAT              2450

GATTAAATCT GAATTCTTAA TAATATATCC TATGCTGATT TTCCCAAAAC              2500

ATGACCCATA GTATTAAATA CATATCATTT TTAAAAATAA AAAAAAACCC              2550

AAAAATAATG CATGCATAAT TTAAATGGTC AATTTATAAA GACAAATCTA              2600

TGAATGAATT TTTCAGTGTT ATCTTCATAT GATATGCTGA ACACCAAAAT              2650

CTCCAGAAAT GCATTTTATG TAGTTCTAAA ATCAGCAAAA TATTGGTATT              2700

ACAAAAATGC AGAATATTTA GTGTGCTACA GATCTGAATT ATAGTTCTAA              2750

TTTATTATTA CTTTTTTTCT AATTTACTGA TCTTACTACT ACAAAGAAAA              2800

AAAAACCCAA CCCATCTGCA ATTCAAATCA GAAAGTTTGG ACAGCTTTAC              2850

AAGTATTAGT GCATGCTCAG AACAGGTGGG ACTAAAACAA ACTCAAGGAA              2900

CTGTTGGCTG TTTTCCCGAT ACTGAGAATT CAACAGCTCC AGAGCAGAAG              2950

CCACAGGGGC ATAGCTTAGT CCAAACTGCT AATTTCATTT TACAGTGTAT              3000

GTAACGCTTA GTCTCACAGT GTCTTTAACT CATCTTTGCA ATCAACAACT              3050

TTACTAGTGA CTTTCTGGAA CAATTTCCTT TCAGGAATAC ATATTCACTG              3100

CTTAGAGGTG ACCTTGCCTT AATATATTTG TGAAGTTAAA ATTTTAAAGA              3150

TAGCTCATGA AACTTTTGCT TAAGCAAAAA GAAAACCTCG AATTGAAATG              3200

TGTGAGGCAA ACTATGCATG GGAATAGCTT AATGTGAAGA TAATCATTTG              3250

GACAACTCAA ATCCATCAAC ATGACCAATG TTTTTCATCT GCCACATCTC              3300

AAAATAAAAC TTCTGGTGAA ACAAATTAAA CAAAATATCC AAACCTCAAA              3350

AAAAA                                                               3355
```

(2) INFORMATION FOR SEQ ID NO: 4:

(i) SEQUENCE CHARACTERISTICS:
        (A) LENGTH: 491 amino acids
        (B) TYPE: Amino Acid
        (D) TOPOLOGY: Linear (xi) SEQUENCE DESCRIPTION: SEQ ID NO: 4:

```
Met Lys Thr Phe Thr Trp Thr Leu Gly Val Leu Phe Phe Leu Leu
 1               5                  10                  15

Val Asp Thr Gly His Cys Arg Gly Gly Gln Phe Lys Ile Lys Lys
                20                  25                  30

Ile Asn Gln Arg Arg Tyr Pro Arg Ala Thr Asp Gly Lys Glu Glu
                35                  40                  45

Ala Lys Lys Cys Ala Tyr Thr Phe Leu Val Pro Glu Gln Arg Ile
                50                  55                  60

Thr Gly Pro Ile Cys Val Asn Thr Lys Gly Gln Asp Ala Ser Thr
                65                  70                  75

Ile Lys Asp Met Ile Thr Arg Met Asp Leu Glu Asn Leu Lys Asp
                80                  85                  90

Val Leu Ser Arg Gln Lys Arg Glu Ile Asp Val Leu Gln Leu Val
```

-continued

```
                            95                  100                 105
Val Asp Val Asp Gly Asn Ile Val Asn Glu Val Lys Leu Leu Arg
                110                 115                 120
Lys Glu Ser Arg Asn Met Asn Ser Arg Val Thr Gln Leu Tyr Met
                125                 130                 135
Gln Leu Leu His Glu Ile Ile Arg Lys Arg Asp Asn Ser Leu Glu
                140                 145                 150
Leu Ser Gln Leu Glu Asn Lys Ile Leu Asn Val Thr Thr Glu Met
                155                 160                 165
Leu Lys Met Ala Thr Arg Tyr Arg Glu Leu Glu Val Lys Tyr Ala
                170                 175                 180
Ser Leu Thr Asp Leu Val Asn Asn Gln Ser Val Met Ile Thr Leu
                185                 190                 195
Leu Glu Glu Gln Cys Leu Arg Ile Phe Ser Arg Gln Asp Thr His
                200                 205                 210
Val Ser Pro Pro Leu Val Gln Val Val Pro Gln His Ile Pro Asn
                215                 220                 225
Ser Gln Gln Tyr Thr Pro Gly Leu Leu Gly Asn Glu Ile Gln
                230                 235                 240
Arg Asp Pro Gly Tyr Pro Arg Asp Leu Met Pro Pro Asp Leu
                245                 250                 255
Ala Thr Ser Pro Thr Lys Ser Pro Phe Lys Ile Pro Pro Val Thr
                260                 265                 270
Phe Ile Asn Glu Gly Pro Phe Lys Asp Cys Gln Gln Ala Lys Glu
                275                 280                 285
Ala Gly His Ser Val Ser Gly Ile Tyr Met Ile Lys Pro Glu Asn
                290                 295                 300
Ser Asn Gly Pro Met Gln Leu Trp Cys Glu Asn Ser Leu Asp Pro
                305                 310                 315
Gly Gly Trp Thr Val Ile Gln Lys Arg Thr Asp Gly Ser Val Asn
                320                 325                 330
Phe Phe Arg Asn Trp Glu Asn Tyr Lys Lys Gly Phe Gly Asn Ile
                335                 340                 345
Asp Gly Glu Tyr Trp Leu Gly Leu Glu Asn Ile Tyr Met Leu Ser
                350                 355                 360
Asn Gln Asp Asn Tyr Lys Leu Leu Ile Glu Leu Glu Asp Trp Ser
                365                 370                 375
Asp Lys Lys Val Tyr Ala Glu Tyr Ser Ser Phe Arg Leu Glu Pro
                380                 385                 390
Glu Ser Glu Phe Tyr Arg Leu Arg Leu Gly Thr Tyr Gln Gly Asn
                395                 400                 405
Ala Gly Asp Ser Met Met Trp His Asn Gly Lys Gln Phe Thr Thr
                410                 415                 420
Leu Asp Arg Asp Lys Asp Met Tyr Ala Gly Asn Cys Ala His Phe
                425                 430                 435
His Lys Gly Gly Trp Trp Tyr Asn Ala Cys Ala His Ser Asn Leu
                440                 445                 450
Asn Gly Val Trp Tyr Arg Gly Gly His Tyr Arg Ser Lys His Gln
                455                 460                 465
Asp Gly Ile Phe Trp Ala Glu Tyr Arg Gly Gly Ser Tyr Ser Leu
                470                 475                 480
Arg Ala Val Gln Met Met Ile Lys Pro Ile Asp
                485                 490 491
```

(2) INFORMATION FOR SEQ ID NO: 5:

(i) SEQUENCE CHARACTERISTICS:
        (A) LENGTH: 1780 base pairs
        (B) TYPE: Nucleic Acid
        (C) STRANDEDNESS: Single
        (D) TOPOLOGY: Linear (xi) SEQUENCE DESCRIPTION: SEQ ID NO: 5:

| | | | | |
|---|---|---|---|---|
| GGCTCAGAGG | CCCCACTGGA | CCCTCGGCTC | TTCCTTGGAC | TTCTTGTGTG | 50 |
| TTCTGTGAGC | TTCGCTGGAT | TCAGGGTCTT | GGGCATCAGA | GGTGAGAGGG | 100 |
| TGGGAAGGTC | CGCCGCGATG | GGAAGCCCT | GGCTGCGTGC | GCTACAGCTG | 150 |
| CTGCTCCTGC | TGGGCGCGTC | GTGGGCGCGG | GCGGGCGCCC | CGCGCTGCAC | 200 |
| CTACACCTTC | GTGCTGCCCC | CGCAGAAGTT | CACGGGCGCT | GTGTGCTGGA | 250 |
| GCGGCCCCGC | ATCCACGCGG | GCGACGCCCG | AGGCCGCCAA | CGCCAGCGAG | 300 |
| CTGGCGGCGC | TGCGCATGCG | CGTCGGCCGC | CACGAGGAGC | TGTTACGCGA | 350 |
| GCTGCAGAGG | CTGGCGGCGG | CCGACGGCGC | CGTGGCCGGC | GAGGTGCGCG | 400 |
| CGCTGCGCAA | GGAGAGCCGC | GGCCTGAGCG | CGCGCCTGGG | CCAGTTGCGC | 450 |
| GCGCAGCTGC | AGCACGAGGC | GGGGCCCGGG | GCGGGCCCGG | GGGCGGATCT | 500 |
| GGGGGCGGAG | CCTGCCGCGG | CGCTGGCGCT | GCTCGGGGAG | CGCGTGCTCA | 550 |
| ACGCGTCCGC | CGAGGCTCAG | CGCGCAGCCG | CCCGGTTCCA | CCAGCTGGAC | 600 |
| GTCAAGTTCC | GCGAGCTGGC | GCAGCTCGTC | ACCCAGCAGA | GCAGTCTCAT | 650 |
| CGCCCGCCTG | GAGCGCCTGT | GCCCGGGAGG | CGCGGGCGGG | CAGCAGCAGG | 700 |
| TCCTGCCGCC | ACCCCCACTG | GTGCCTGTGG | TTCCGGTCCG | TCTTGTGGGT | 750 |
| AGCACCAGTG | ACACCAGTAG | GATGCTGGAC | CCAGCCCCAG | AGCCCCAGAG | 800 |
| AGACCAGACC | CAGAGACAGC | AGGAGCCCAT | GGCTTCTCCC | ATGCCTGCAG | 850 |
| GTCACCCTGC | GGTCCCCACC | AAGCCTGTGG | GCCCGTGGCA | GGATTGTGCA | 900 |
| GAGGCCCGCC | AGGCAGGCCA | TGAACAGAGT | GGAGTGTATG | AACTGCGAGT | 950 |
| GGGCCGTCAC | GTAGTGTCAG | TATGGTGTGA | GCAGCAACTG | GAGGGTGGAG | 1000 |
| GCTGGACTGT | GATCCAGCGG | AGGCAAGATG | GTTCAGTCAA | CTTCTTCACT | 1050 |
| ACCTGGCAGC | ACTATAAGGC | GGGCTTTGGG | CGGCCAGACG | GAGAATACTG | 1100 |
| GCTGGGCCTT | GAACCCGTGT | ATCAGCTGAC | CAGCCGTGGG | GACCATGAGC | 1150 |
| TGCTGGTTCT | CCTGGAGGAC | TGGGGGGGCC | GTGGAGCACG | TGCCCACTAT | 1200 |
| GATGGCTTCT | CCCTGGAACC | CGAGAGCGAC | CACTACCGCC | TGCGGCTTGG | 1250 |
| CCAGTACCAT | GGTGATGCTG | GAGACTCTCT | TTCCTGGCAC | AATGACAAGC | 1300 |
| CCTTCAGCAC | CGTGGATAGG | GACCGAGACT | CCTATTCTGG | TAACTGTGCC | 1350 |
| CTGTACCAGC | GGGGAGGCTG | GTGGTACCAT | GCCTGTGCCC | ACTCCAACCT | 1400 |
| CAACGGTGTG | TGGCACCACG | GCGGCCACTA | CCGAAGCCGC | TACCAGGATG | 1450 |
| GTGTCTACTG | GGCTGAGTTT | CGTGGTGGGG | CATATTCTCT | CAGGAAGGCC | 1500 |
| GCCATGCTCA | TTCGGCCCCT | GAAGCTGTGA | CTCTGTGTTC | CTCTGTCCCC | 1550 |
| TAGGCCCTAG | AGGACATTGG | TCAGCAGGAG | CCCAAGTTGT | TCTGGCCACA | 1600 |
| CCTTCTTTGT | GGCTCAGTGC | CAATGTGTCC | CACAGAACTT | CCCACTGTGG | 1650 |
| ATCTGTGACC | CTGGGCGCTG | AAAATGGGAC | CCAGGAATCC | CCCCCGTCAA | 1700 |

```
TATCTTGGCC TCAGATGGCT CCCCAAGGTC ATTCATATCT CGGTTTGAGC         1750

TCATATCTTA TAATAACACA AAGTAGCCAC                              1780
```

(2) INFORMATION FOR SEQ ID NO: 6:

(i) SEQUENCE CHARACTERISTICS:
        (A) LENGTH: 470 amino acids
        (B) TYPE: Amino Acid
        (D) TOPOLOGY: Linear (xi) SEQUENCE DESCRIPTION: SEQ ID NO: 6:

```
Met Gly Lys Pro Trp Leu Arg Ala Leu Gln Leu Leu Leu Leu
 1               5                  10                  15

Gly Ala Ser Trp Ala Arg Ala Gly Ala Pro Arg Cys Thr Tyr Thr
                20                  25                  30

Phe Val Leu Pro Pro Gln Lys Phe Thr Gly Ala Val Cys Trp Ser
                35                  40                  45

Gly Pro Ala Ser Thr Arg Ala Thr Pro Glu Ala Ala Asn Ala Ser
                50                  55                  60

Glu Leu Ala Ala Leu Arg Met Arg Val Gly Arg His Glu Glu Leu
                65                  70                  75

Leu Arg Glu Leu Gln Arg Leu Ala Ala Ala Asp Gly Ala Val Ala
                80                  85                  90

Gly Glu Val Arg Ala Leu Arg Lys Glu Ser Arg Gly Leu Ser Ala
                95                  100                 105

Arg Leu Gly Gln Leu Arg Ala Gln Leu Gln His Glu Ala Gly Pro
                110                 115                 120

Gly Ala Gly Pro Gly Ala Asp Leu Gly Ala Glu Pro Ala Ala Ala
                125                 130                 135

Leu Ala Leu Leu Gly Glu Arg Val Leu Asn Ala Ser Ala Glu Ala
                140                 145                 150

Gln Arg Ala Ala Ala Arg Phe His Gln Leu Asp Val Lys Phe Arg
                155                 160                 165

Glu Leu Ala Gln Leu Val Thr Gln Gln Ser Ser Leu Ile Ala Arg
                170                 175                 180

Leu Glu Arg Leu Cys Pro Gly Gly Ala Gly Gln Gln Gln Val
                185                 190                 195

Leu Pro Pro Pro Leu Val Pro Val Val Pro Val Arg Leu Val
                200                 205                 210

Gly Ser Thr Ser Asp Thr Ser Arg Met Leu Asp Pro Ala Pro Glu
                215                 220                 225

Pro Gln Arg Asp Gln Thr Gln Arg Gln Glu Pro Met Ala Ser
                230                 235                 240

Pro Met Pro Ala Gly His Pro Ala Val Pro Thr Lys Pro Val Gly
                245                 250                 255

Pro Trp Gln Asp Cys Ala Glu Ala Arg Gln Ala Gly His Glu Gln
                260                 265                 270

Ser Gly Val Tyr Glu Leu Arg Val Gly Arg His Val Val Ser Val
                275                 280                 285

Trp Cys Glu Gln Gln Leu Glu Gly Gly Gly Trp Thr Val Ile Gln
                290                 295                 300

Arg Arg Gln Asp Gly Ser Val Asn Phe Phe Thr Thr Trp Gln His
                305                 310                 315

Tyr Lys Ala Gly Phe Gly Arg Pro Asp Gly Glu Tyr Trp Leu Gly
```

```
            320                 325                 330
Leu Glu Pro Val Tyr Gln Leu Thr Ser Arg Gly Asp His Glu Leu
            335                 340                 345
Leu Val Leu Leu Glu Asp Trp Gly Gly Arg Gly Ala Arg Ala His
            350                 355                 360
Tyr Asp Gly Phe Ser Leu Glu Pro Glu Ser Asp His Tyr Arg Leu
            365                 370                 375
Arg Leu Gly Gln Tyr His Gly Asp Ala Gly Asp Ser Leu Ser Trp
            380                 385                 390
His Asn Asp Lys Pro Phe Ser Thr Val Asp Arg Asp Arg Asp Ser
            395                 400                 405
Tyr Ser Gly Asn Cys Ala Leu Tyr Gln Arg Gly Gly Trp Trp Tyr
            410                 415                 420
His Ala Cys Ala His Ser Asn Leu Asn Gly Val Trp His His Gly
            425                 430                 435
Gly His Tyr Arg Ser Arg Tyr Gln Asp Gly Val Tyr Trp Ala Glu
            440                 445                 450
Phe Arg Gly Gly Ala Tyr Ser Leu Arg Lys Ala Ala Met Leu Ile
            455                 460                 465
Arg Pro Leu Lys Leu
            470

(2) INFORMATION FOR SEQ ID NO: 7:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO: 7:

GCTGACGAAC CAAGGCAACT ACAAACTCCT GGT                           33

(2) INFORMATION FOR SEQ ID NO: 8:

(i) SEQUENCE CHARACTERISTICS:
        (A) LENGTH: 41 base pairs
        (B) TYPE: Nucleic Acid
        (C) STRANDEDNESS: Single
        (D) TOPOLOGY: Linear (xi) SEQUENCE DESCRIPTION: SEQ ID NO: 8:

TGCGGCCGGA CCAGTCCTCC ATGGTCACCA GGAGTTTGTA G                  41

(2) INFORMATION FOR SEQ ID NO: 9:

(i) SEQUENCE CHARACTERISTICS:
        (A) LENGTH: 33 base pairs
        (B) TYPE: Nucleic Acid
        (C) STRANDEDNESS: Single
        (D) TOPOLOGY: Linear (xi) SEQUENCE DESCRIPTION: SEQ ID NO: 9:

GGTGGTGAAC TGCTTGCCGT TGTGCCATGT AAA                           33

(2) INFORMATION FOR SEQ ID NO: 10:

(i) SEQUENCE CHARACTERISTICS:
        (A) LENGTH: 29 base pairs
        (B) TYPE: Nucleic Acid
        (C) STRANDEDNESS: Single
        (D) TOPOLOGY: Linear
```

(xi) SEQUENCE DESCRIPTION: SEQ ID NO: 10:

CAGGTTATCC CAGAGATTTA ATGCCACCA                                              29

(2) INFORMATION FOR SEQ ID NO: 11:

(i) SEQUENCE CHARACTERISTICS:
        (A) LENGTH: 34 base pairs
        (B) TYPE: Nucleic Acid
        (C) STRANDEDNESS: Single
        (D) TOPOLOGY: Linear (xi) SEQUENCE DESCRIPTION: SEQ ID NO: 11:

TTGGTGGGAG AAGTTGCCAG ATCAGGTGGT GGCA                                        34

(2) INFORMATION FOR SEQ ID NO: 12:

(i) SEQUENCE CHARACTERISTICS:
        (A) LENGTH: 25 base pairs
        (B) TYPE: Nucleic Acid
        (C) STRANDEDNESS: Single
        (D) TOPOLOGY: Linear (xi) SEQUENCE DESCRIPTION: SEQ ID NO: 12:

TTCACACCAT AACTGCATTG GTCCA                                                  25

(2) INFORMATION FOR SEQ ID NO: 13:

(i) SEQUENCE CHARACTERISTICS:
        (A) LENGTH: 34 base pairs
        (B) TYPE: Nucleic Acid
        (C) STRANDEDNESS: Single
        (D) TOPOLOGY: Linear (xi) SEQUENCE DESCRIPTION: SEQ ID NO: 13:

ACGTAGTTCC AGTATGGTGT GAGCAGCAAC TGGA                                        34

(2) INFORMATION FOR SEQ ID NO: 14:

(i) SEQUENCE CHARACTERISTICS:
        (A) LENGTH: 26 base pairs
        (B) TYPE: Nucleic Acid
        (C) STRANDEDNESS: Single
        (D) TOPOLOGY: Linear (xi) SEQUENCE DESCRIPTION: SEQ ID NO: 14:

AGTCCAGCCT CCACCCTCCA GTTGCT                                                 26

(2) INFORMATION FOR SEQ ID NO: 15:

(i) SEQUENCE CHARACTERISTICS:
        (A) LENGTH: 25 base pairs
        (B) TYPE: Nucleic Acid
        (C) STRANDEDNESS: Single
        (D) TOPOLOGY: Linear (xi) SEQUENCE DESCRIPTION: SEQ ID NO: 15:

CCCCAGTCCT CCAGGAGAAC CAGCA                                                  25

(2) INFORMATION FOR SEQ ID NO: 16:

(i) SEQUENCE CHARACTERISTICS:
        (A) LENGTH: 2042 base pairs
        (B) TYPE: Nucleic Acid
        (C) STRANDEDNESS: Single
        (D) TOPOLOGY: Linear (xi) SEQUENCE DESCRIPTION: SEQ ID NO: 16:

| | | |
|---|---|---|
| GCGGACGCGT GGGTGAAATT GAAAATCAAG ATAAAAATGT TCACAATTAA | 50 |
| GCTCCTTCTT TTTATTGTTC CTCTAGTTAT TTCCTCCAGA ATTGATCAAG | 100 |
| ACAATTCATC ATTTGATTCT CTATCTCCAG AGCCAAAATC AAGATTTGCT | 150 |
| ATGTTAGACG ATGTAAAAAT TTTAGCCAAT GGCCTCCTTC AGTTGGGACA | 200 |
| TGGTCTTAAA GACTTTGTCC ATAAGACGAA GGGCCAAATT AATGACATAT | 250 |
| TTCAAAAACT CAACATATTT GATCAGTCTT TTTATGATCT ATCGCTGCAA | 300 |
| ACCAGTGAAA TCAAAGAAGA AGAAAAGGAA CTGAGAAGAA CTACATATAA | 350 |
| ACTACAAGTC AAAAATGAAG AGGTAAAGAA TATGTCACTT GAACTCAACT | 400 |
| CAAAACTTGA AAGCCTCCTA GAAGAAAAAA TTCTACTTCA ACAAAAAGTG | 450 |
| AAATATTTAG AAGAGCAACT AACTAACTTA ATTCAAAATC AACCTGAAAC | 500 |
| TCCAGAACAC CCAGAAGTAA CTTCACTTAA AACTTTTGTA GAAAAACAAG | 550 |
| ATAATAGCAT CAAAGACCTT CTCCAGACCG TGGAAGACCA ATATAAACAA | 600 |
| TTAAACCAAC AGCATAGTCA AATAAAAGAA ATAGAAAATC AGCTCAGAAG | 650 |
| GACTAGTATT CAAGAACCCA CAGAAATTTC TCTATCTTCC AAGCCAAGAG | 700 |
| CACCAAGAAC TACTCCCTTT CTTCAGTTGA ATGAAATAAG AAATGTAAAA | 750 |
| CATGATGGCA TTCCTGCTGA ATGTACCACC ATTTATAACA GAGGTGAACA | 800 |
| TACAAGTGGC ATGTATGCCA TCAGACCCAG CAACTCTCAA GTTTTTCATG | 850 |
| TCTACTGTGA TGTTATATCA GGTAGTCCAT GGACATTAAT TCAACATCGA | 900 |
| ATAGATGGAT CACAAAACTT CAATGAAACG TGGGAGAACT ACAAATATGG | 950 |
| TTTTGGGAGG CTTGATGGAG AATTTTGGTT GGGCCTAGAG AAGATATACT | 1000 |
| CCATAGTGAA GCAATCTAAT TATGTTTTAC GAATTGAGTT GGAAGACTGG | 1050 |
| AAAGACAACA AACATTATAT TGAATATTCT TTTTACTTGG GAAATCACGA | 1100 |
| AACCAACTAT ACGCTACATC TAGTTGCGAT TACTGGCAAT GTCCCCAATG | 1150 |
| CAATCCCGGA AAACAAAGAT TTGGTGTTTT CTACTTGGGA TCACAAAGCA | 1200 |
| AAAGGACACT TCAACTGTCC AGAGGGTTAT TCAGGAGGCT GGTGGTGGCA | 1250 |
| TGATGAGTGT GGAGAAAACA ACCTAAATGG TAAATATAAC AAACCAAGAG | 1300 |
| CAAAATCTAA GCCAGAGAGG AGAAGAGGAT TATCTTGGAA GTCTCAAAAT | 1350 |
| GGAAGGTTAT ACTCTATAAA ATCAACCAAA ATGTTGATCC ATCCAACAGA | 1400 |
| TTCAGAAAGC TTTGAATGAA CTGAGGCAAT TTAAAGGCAT ATTTAACCAT | 1450 |
| TAACTCATTC CAAGTTAATG TGGTCTAATA ATCTGGTATA AATCCTTAAG | 1500 |
| AGAAAGCTTG AGAAATAGAT TTTTTTTATC TTAAAGTCAC TGTCTATTTA | 1550 |
| AGATTAAACA TACAATCACA TAACCTTAAA GAATACCGTT TACATTTCTC | 1600 |
| AATCAAAATT CTTATAATAC TATTTGTTTT AAATTTGTG ATGTGGGAAT | 1650 |
| CAATTTTAGA TGGTCACAAT CTAGATTATA ATCAATAGGT GAACTTATTA | 1700 |
| AATAACTTTT CTAAATAAAA AATTTAGAGA CTTTTATTTT AAAAGGCATC | 1750 |
| ATATGAGCTA ATATCACAAC TTTCCCAGTT TAAAAAACTA GTACTCTTGT | 1800 |
| TAAAACTCTA AACTTGACTA AATACAGAGG ACTGGTAATT GTACAGTTCT | 1850 |
| TAAATGTTGT AGTATTAATT TCAAAACTAA AAATCGTCAG CACAGAGTAT | 1900 |
| GTGTAAAAAT CTGTAATACA AATTTTTAAA CTGATGCTTC ATTTTGCTAC | 1950 |

```
AAAATAATTT GGAGTAAATG TTTGATATGA TTTATTTATG AAACCTAATG          2000

AAGCAGAATT AAATACTGTA TTAAAATAAG TTCGCTGTCT TT                 2042
```

(2) INFORMATION FOR SEQ ID NO: 17:

(i) SEQUENCE CHARACTERISTICS:
        (A) LENGTH: 460 amino acids
        (B) TYPE: Amino Acid
        (D) TOPOLOGY: Linear (xi) SEQUENCE DESCRIPTION: SEQ ID NO: 17:

```
Met Phe Thr Ile Lys Leu Leu Leu Phe Ile Val Pro Leu Val Ile
 1               5                  10                  15

Ser Ser Arg Ile Asp Gln Asp Asn Ser Ser Phe Asp Ser Leu Ser
                20                  25                  30

Pro Glu Pro Lys Ser Arg Phe Ala Met Leu Asp Asp Val Lys Ile
                35                  40                  45

Leu Ala Asn Gly Leu Leu Gln Leu Gly His Gly Leu Lys Asp Phe
                50                  55                  60

Val His Lys Thr Lys Gly Gln Ile Asn Asp Ile Phe Gln Lys Leu
                65                  70                  75

Asn Ile Phe Asp Gln Ser Phe Tyr Asp Leu Ser Leu Gln Thr Ser
                80                  85                  90

Glu Ile Lys Glu Glu Glu Lys Glu Leu Arg Arg Thr Thr Tyr Lys
                95                 100                 105

Leu Gln Val Lys Asn Glu Glu Val Lys Asn Met Ser Leu Glu Leu
               110                 115                 120

Asn Ser Lys Leu Glu Ser Leu Leu Glu Glu Lys Ile Leu Leu Gln
               125                 130                 135

Gln Lys Val Lys Tyr Leu Glu Glu Gln Leu Thr Asn Leu Ile Gln
               140                 145                 150

Asn Gln Pro Glu Thr Pro Glu His Pro Glu Val Thr Ser Leu Lys
               155                 160                 165

Thr Phe Val Glu Lys Gln Asp Asn Ser Ile Lys Asp Leu Leu Gln
               170                 175                 180

Thr Val Glu Asp Gln Tyr Lys Gln Leu Asn Gln Gln His Ser Gln
               185                 190                 195

Ile Lys Glu Ile Glu Asn Gln Leu Arg Arg Thr Ser Ile Gln Glu
               200                 205                 210

Pro Thr Glu Ile Ser Leu Ser Ser Lys Pro Arg Ala Pro Arg Thr
               215                 220                 225

Thr Pro Phe Leu Gln Leu Asn Glu Ile Arg Asn Val Lys His Asp
               230                 235                 240

Gly Ile Pro Ala Glu Cys Thr Thr Ile Tyr Asn Arg Gly Glu His
               245                 250                 255

Thr Ser Gly Met Tyr Ala Ile Arg Pro Ser Asn Ser Gln Val Phe
               260                 265                 270

His Val Tyr Cys Asp Val Ile Ser Gly Ser Pro Trp Thr Leu Ile
               275                 280                 285

Gln His Arg Ile Asp Gly Ser Gln Asn Phe Asn Glu Thr Trp Glu
               290                 295                 300

Asn Tyr Lys Tyr Gly Phe Gly Arg Leu Asp Gly Glu Phe Trp Leu
               305                 310                 315

Gly Leu Glu Lys Ile Tyr Ser Ile Val Lys Gln Ser Asn Tyr Val
```

-continued

```
                      320                     325                     330
Leu Arg Ile Glu Leu Glu Asp Trp Lys Asp Asn Lys His Tyr Ile
                335                     340                     345
Glu Tyr Ser Phe Tyr Leu Gly Asn His Glu Thr Asn Tyr Thr Leu
                350                     355                     360
His Leu Val Ala Ile Thr Gly Asn Val Pro Asn Ala Ile Pro Glu
                365                     370                     375
Asn Lys Asp Leu Val Phe Ser Thr Trp Asp His Lys Ala Lys Gly
                380                     385                     390
His Phe Asn Cys Pro Glu Gly Tyr Ser Gly Gly Trp Trp Trp His
                395                     400                     405
Asp Glu Cys Gly Glu Asn Asn Leu Asn Gly Lys Tyr Asn Lys Pro
                410                     415                     420
Arg Ala Lys Ser Lys Pro Glu Arg Arg Arg Gly Leu Ser Trp Lys
                425                     430                     435
Ser Gln Asn Gly Arg Leu Tyr Ser Ile Lys Ser Thr Lys Met Leu
                440                     445                     450
Ile His Pro Thr Asp Ser Glu Ser Phe Glu
                455                     460
```

TIE LIGAND HOMOLOGUES

This is a divisional of application Ser. No. 08/933,821 filed on Sep. 19, 1997, now U.S. Pat. No. 5,972,338, which application is incorporated herein by reference and to application priority is claimed under 35 USC §120.

FIELD OF THE INVENTION

The present invention concerns isolated nucleic acid molecules encoding novel TIE ligand homologues the TIE proteins encoded by such nucleic acid molecules, as well as methods and means for making and using such nucleic acid and protein molecules.

BACKGROUND ART

The abbreviations "TIE" or "tie" are acronyms, which stand for "tyrosine kinase containing Ig and EGF homology domains" and were coined to designate a new family of receptor tyrosine kinases which are almost exclusively expressed in vascular endothelial cells and early hemopoietic cells, and are characterized by the presence of an EGF-like domain, and extracellular folding units stabilized by intra-chain disulfide bonds, generally referred to as "immunoglobulin (IG)-like" folds. A tyrosine kinase homologous cDNA fragment from human leukemia cells (tie) was described by Partanen et al., Proc. Natl. Acad. Sci. USA 87, 8913–8917 (1990). The mRNA of this human "tie" receptor has been detected in all human fetal and mouse embryonic tissues, and has been reported to be localized in the cardiac and vascular endothelial cells. Korhonen et al., Blood 80, 2548–2555 (1992); PCT Application Publication No. WO 93/14124 (published Jul. 22, 1993). The rat homolog of human tie, referred to as "tie-1", was identified by Maisonpierre et al., Oncogene 8, 1631–1637 (1993)). Another tie receptor, designated "tie-2" was originally identified in rats (Dumont et al., Oncogene 8, 1293–1301 (1993)), while the human homolog of tie-2, referred to as "ork" was described in U.S. Pat. No. 5,447,860 (Ziegler). The murine homolog of tie-2 was originally termed "tek." The cloning of a mouse tie-2 receptor from a brain capillary cDNA library is disclosed in PCT Application Publication No. WO 95/13387 (published May 18, 1995). The TIE receptors are believed to be actively involved in angiogenesis, and may play a role in hemopoiesis as well.

The expression cloning of human TIE-2 ligands has been described in PCT Application Publication No. WO 96/11269 (published Apr. 18, 1996) and in U.S. Pat. No. 5,521,073 (published May 28, 1996). A vector designated as λgt10 encoding a TIE-2 ligand named "htie-2 ligand 1" or "hTL1" has been deposited under ATCC Accession No. 75928. A plasmid encoding another TIE-2 ligand designated "htie-2 2" or "hTL2" is available under ATCC Accession No. 75928. This second ligand has been described as an antagonist of the TIE-2 receptor. The identification of secreted human and mouse ligands for the TIE-2 receptor has been reported by Davis et al., Cell 87, 1161–1169 (1996). The human ligand designated "Angiopoietin-1", to reflect its role in angiogenesis and potential action during hemopoiesis, is the same ligand as the ligand variously designated as "htie-2 1" or "hTL-1" in WO 96/11269. Angiopoietin-1 has been described to play an angiogenic role later and distinct from that of VEGF (Suri et al., Cell 87, 1171–1180 (1996)). Since TIE-2 is apparently upregulated during the pathologic angiogenesis requisite for tumor growth (Kaipainen et al., Cancer Res. 54, 6571–6577 (1994)) angiopoietin-1 has been suggested to be additionally useful for specifically targeting tumor vasculature (Davis et al., supra).

SUMMARY OF THE INVENTION

The present invention concerns novel human TIE ligand homologues with powerful effects on vasculature. The invention also provides for isolated nucleic acid molecules encoding such ligands or functional derivatives thereof, and vectors containing such nucleic acid molecules. The invention further concerns host cells transformed with such nucleic acid to produce the novel TIE ligand homologues or functional derivatives thereof. The novel ligands may be agonists or antagonists of TIE receptors, known or hereinafter discovered. Their therapeutic or diagnostic use, including the delivery of other therapeutic or diagnostic agents to cells expressing the respective TIE receptors, is also within the scope of the present invention.

The present invention further provides for agonist or antagonist antibodies specifically binding the TIE ligand homologues herein, and the diagnostic or therapeutic use of such antibodies.

In another aspect, the invention concerns compositions comprising the novel ligands or antibodies.

In a further aspect, the invention concerns conjugates of the novel TIE ligand homologues of the present invention with other therapeutic or cytotoxic agents, and compositions comprising such conjugates. Because the TIE-2 receptor has been reported to be upregulated during the pathologic angiogenesis that is requisite for tumor growth, the conjugates of the TIE ligands of the present invention to cytotoxic or other anti-tumor agents are useful in specifically targeting tumor vasculature.

In yet another aspect, the invention concerns a method for identifying a cell that expresses a TIE (e.g. TIE-2) receptor, which comprises contacting a cell with a detectably labeled TIE ligand homologues of the present invention under conditions permitting the binding of such TIE ligand to the TIE receptor, and determining whether such binding has indeed occurred.

In a different aspect, the invention concerns a method for measuring the amount of a TIE ligand homologues of the present invention in a biological sample by contacting the biological sample with at least one antibody specifically binding the TIE ligand, and measuring the amount of the TIE ligand-antibody complex formed.

The invention further concerns a screening method for identifying polypeptide or small molecule agonists or antagonists of a TIE receptor based upon their ability to compete with a native or variant TIE ligand of the present invention for binding to a corresponding TIE receptor.

The invention also concerns a method for imaging the presence of angiogenesis in wound healing, in inflammation or in tumors of human patients, which comprises administering detectably labeled TIE ligands or agonist antibodies of the present invention, and detecting angiogenesis.

In another aspect, the invention concerns a method of promoting or inhibiting neovascularization in a patient by administering an effective amount of a TIE ligand homologues of the present invention in a pharmaceutically acceptable vehicle. In a preferred embodiment, the present invention concerns a method for the promotion of wound healing. In another embodiment, the invention concerns a method for promoting angiogenic processes, such as for inducing collateral vascularization in an ischemic heart or limb. In a further preferred embodiment, the invention concerns a method for inhibiting tumor growth.

In yet another aspect, the invention concerns a method of promoting bone development and/or maturation and/or growth in a patient, comprising administering to the patient an effective amount of a TIE ligand homologues of the present invention in a pharmaceutically acceptable vehicle.

In a further aspect, the invention concerns a method of promoting muscle growth and development, which comprises administering a patient in need an effective amount of a TIE ligand homologues of the present invention in a pharmaceutically acceptable vehicle.

The TIE ligand homologues of the present invention may be administered alone, or in combination with each other and/or with other therapeutic or diagnostic agents, including members of the VEGF family. Combinations therapies may lead to new approaches for promoting or inhibiting neovascularization, and muscle growth and development.

BRIEF DESCRIPTION OF THE FIGURES

FIGS. 1A-1 and 1A-2 show the nucleotide sequence of FLS139 (SEQ ID NO: 16).

FIGS. 1B-1 and 1B-2 show the amino acid sequence of FLS139 (SEQ ID NO: 17).

FIGS. 2A and 2B show the nucleotide sequence of the TIE ligand homologue NL1 (SEQ ID NO: 1) (DNA 22779).

FIGS. 3A and 3B show the amino acid sequence of the TIE ligand homologue NL1 (SEQ ID NO:2).

FIGS. 4A, 4B and 4C show the nucleotide sequence of the TIE ligand homologue NL5 (SEQ ID NO: 3) (DNA 28497).

FIGS. 5A and 5B show the amino acid sequence of the TIE ligand homologue NL5 (SEQ ID NO: 4).

FIGS. 6A and 6B show the nucleotide sequence of the TIE ligand homologue NL8 (SEQ ID NO: 5) (DNA 23339).

FIGS. 7A and 7B show the amino acid sequence of the TIE ligand homologue NL8 (SEQ ID NO:6).

DETAILED DESCRIPTION OF THE INVENTION

A. TIE LIGAND HOMOLOGUES AND NUCLEIC ACID MOLECULES ENCODING THEM

Figure 8A:
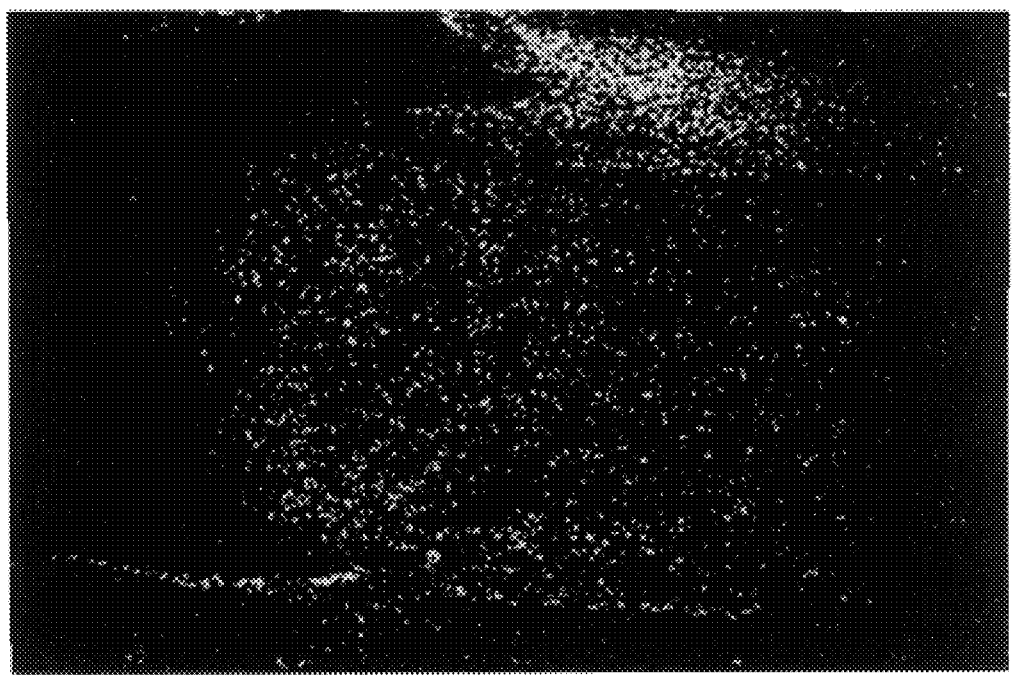
FIGS. 8A and 8B show the expression of NL1 in various tissues as determined by in situ hybridization to cellular RNA.

The TIE ligand homologues of the present invention include the native human ligands designated NL1 (SEQ. ID. NO: 2), NL5 (SEQ. ID. NO: 4), and NL8 (SEQ. ID. NO: 6), their homologs in other, non-human mammalian species, including, but not limited to, higher mammals, such as monkey; rodents, such as mice, rats, hamster; porcine; equine; bovine; naturally occurring allelic and splice variants, and biologically active (functional) derivatives, such as, amino acid sequence variants of such native molecules, as long as they differ from a native TL-1 or TL-2 ligand. The nativeTIE ligand homologues of the present invention are substantially free of other proteins with which they are associated in their native environment. This definition is not limited in any way by the method(s) by which the TIE ligand homologues of the present invention are obtained, and includes all ligands otherwise within the definition, whether purified from natural source, obtained by recombinant DNA technology, synthesized, or prepared by any combination of these and/or other techniques. The amino acid sequence variants of the native TIE ligand homologues of the present invention shall have at least about 90%, preferably, at least about 95%, more preferably at least about 98%, most preferably at least about 99% sequence identity with a full-length, native human TIE ligand homologues of the present invention, or with the fibrinogen-like domain of a native human TIE ligand homologues of the present invention. Such amino acid sequence variants preferably exhibit or inhibit a qualitative biological activity of a native TIE ligand homologues.

The term "fibrinogen domain" or "fibrinogen-like domain" is used to refer to amino acids from about position 278 to about position 498 in the known hTL-1 amino acid sequence; amino acids from about position 276 to about position 496 in the known hTL-2 amino acid sequence; amino acids from about position 270 to about 493 in the amino acid sequence of NL1; amino acids from about position 272 to about position 491 in the amino acid sequence of NL5; and amino acids from about position 252 to about position 470 in the amino acid sequence of NL8; and to homologous domains in other TIE ligands.

The term "nucleic acid molecule" includes RNA, DNA and cDNA molecules. It will be understood that, as a result of the degeneracy of the genetic code, a multitude of nucleotide sequences encoding a given TIE ligand may be produced. The present invention specifically contemplates every possible variation of nucleotide sequences, encoding the TIE ligand homologue of the present invention, based upon all possible codon choices. Although nucleic acid molecules which encode the TIE ligand homologues herein are preferably capable of hybridizing, under stringent conditions, to a naturally occurring TIE ligand homologues gene, it may be advantageous to produce nucleotide sequences encoding TIE ligand homologues, which possess a substantially different codon usage. For example, codons may be selected to increase the rate at which expression of the polypeptide occurs in a particular prokaryotic or eukaryotic host cells, in accordance with the frequency with which a particular codon is utilized by the host. In addition, RNA transcripts with improved properties, e.g. half-life can be produced by proper choice of the nucleotide sequences encoding a given TIE ligand homologue.

"Sequence identity" shall be determined by aligning the two sequences to be compared following the Clustal method of multiple sequence alignment (Higgins et al., *Comput. Appl. Biosci.* 5, 151–153 (1989), and Higgins et al., *Gene* 73, 237–244 (1988)) that is incorporated in version 1.6 of the Lasergene biocomputing software (DNASTAR, Inc., Madison, Wis.), or any updated version or equivalent of this software.

The terms "biological activity" and "biologically active" with regard to a TIE ligand homologue of the present invention refer to the ability of a molecule to specifically bind to and signal through a native TIE receptor, e. g. a native TIE-2 receptor, or to block the ability of a native TIE receptor (e.g. TIE-2) to participate in signal transduction. Thus, the (native and variant) TIE ligand homologues of the present invention include agonists and antagonists of a native TIE, e.g. TIE-2, receptor. Preferred biological activities of the TIE ligand homologues of the present invention include the ability to induce or inhibit vascularization. The ability to induce vascularization will be useful for the treatment of biological conditions and diseases, where vascularization is desirable, such as wound healing, ischaemia, and diabetes. On the other hand, the ability to inhibit or block vascularization may, for example, be useful in preventing or attenuating tumor growth. Another preferred biological activity is the ability to affect muscle growth or development. A further preferred biological activity is the ability to influence bone development, maturation, or growth.

The term "functional derivative" is used to define biologically active amino acid sequence variants of the native TIE ligand homologues of the present invention, as well as covalent modifications, including derivatives obtained by reaction with organic derivatizing agents, post-translational modifications, derivatives with nonproteinaceous polymers, and immunoadhesins.

"Vascular endothelial growth factor"/"vascular permeability factor" (VEGF/VPF) is an endothelial cell-specific mitogen which has recently been shown to be stimulated by hypoxia and required for tumor angiogenesis (Senger et al., *Cancer* 46: 5629–5632 (1986); Kim et al., *Nature* 362:841–844 (1993); Schweiki et al., *Nature* 359: 843–845 (1992); Plate et al., *Nature* 359: 845–848 (1992)). It is a 34–43 kDa (with the predominant species at about 45 kDa) dimeric, disulfide-linked glycoprotein synthesized and secreted by a variety of tumor and normal cells. In addition, cultured human retinal cells such as pigment epithelial cells and pericytes have been demonstrated to secrete VEGF and to increase VEGF gene expression in response to hypoxia (Adamis et al.,*Biochem. Biophs. Res. Commun.* 193: 631–638 (1993); Plouet et al., *Invest. Ophthalmol. Vis. Sci.* 34: 900 (1992); Adamis et al., *Invest. Ophthalmol. Vis. Sci.* 34: 1440 (1993); Aiello et al.,*Invest. Opthalmol. Vis. Sci.* 35: 1868 (1994); Simorre-pinatel et al., *Invest. Opthalmol. Vis. Sci.* 35: 3393–3400 (1994)). In contrast, VEGF in normal tissues is relatively low. Thus, VEGF appears to play a principle role in many pathological states and processes related to neovascularization. Regulation of VEGF expression in tissues affected by the various conditions described above could therefore be key in treatment or preventative therapies associated with hypoxia.

The term "isolated" when used to describe the various polypeptides described herein, means polypeptides that have been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the TIE ligand's natural environment will not be present. Ordinarily, however, isolated polypeptide will be prepared by at least one purification step.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes nucleic acid molecules contained in cells that ordinarily express an TIE ligand of the present invention, where, for example, the nucleic acid molecule is in a chromosomal location different from that of natural cells.

The term "amino acid sequence variant" refers to molecules with some differences in their amino acid sequences as compared to a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule. Deletional variants include those having C- and/or N-terminal deletions (truncations) as well as variants with internal deletions of one or more amino acids. The preferred deletional variants of the present invention contain deletions outside the fibrinogen-like domain of a native TIE ligand homologue of the present invention.

The amino acid sequence variants of the present invention may contain various combinations of amino acid substitutions, insertions and/or deletions, to produce molecules with optimal characteristics.

The amino acids may be classified according to the chemical composition and properties of their side chains. They are broadly classified into two groups, charged and uncharged. Each of these groups is divided into subgroups to classify the amino acids more accurately.

I. Charged Amino Acids
  Acidic Residues: aspartic acid, glutamic acid
  Basic Residues: lysine, arginine, histidine II. Uncharged Amino Acids
  Hydrophilic Residues: serine, threonine, asparagine, glutamine
  Aliphatic Residues: glycine, alanine, valine, leucine, isoleucine
  Non-polar Residues: cysteine, methionine, proline
  Aromatic Residues: phenylalanine, tyrosine, tryptophan Conservative substitutions involve exchanging a member within one group for another member within the same group, whereas non-conservative substitutions will entail exchanging a member of one of these classes for another. Variants obtained by non-conservative substitutions are expected to result in significant changes in the biological properties/function of the obtained variant.

Amino acid sequence deletions generally range from about 1 to 30 residues, more preferably about 1 to 10 residues, and typically are contiguous. Deletions may be introduced into regions not directly involved in the interaction with a native TIE receptor. Deletions are preferably performed outside the fibrinogen-like regions at the C-terminus of the TIE ligand homologues of the present invention.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the TIE ligand homologues amino acid sequence) may range generally from about 1 to 10 residues, more preferably 1 to 5 residues, more preferably 1 to 3 residues. Examples of terminal insertions include the TIE ligand homologues with an N-terminal methionyl residue, an artifact of its direct expression in bacterial recombinant cell culture, and fusion of a heterologous N-terminal signal sequence to the N-terminus of the TIE ligand homologues molecule to facilitate the secretion of the mature TIE ligand homologues from recombinant host cells. Such signal sequences will generally be obtained from, and thus homologous to, the intended host cell species. Suitable sequences include, for example, STII or Ipp for *E. coli*, alpha factor for yeast, and viral signals such as herpes gD for mammalian cells. Other insertional variants of the native TIE ligand homologues molecules include the fusion of the N- or C-terminus of the TIE ligand homologues molecule to immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions), albumin, or ferritin, as described in WO 89/02922 published on Apr. 6, 1989.

Since it is often difficult to predict in advance the characteristics of a variant TIE ligand homologue, it will be appreciated that some screening will be needed to select the optimum variant.

Amino acid sequence variants of native TIE ligand homologues of the present invention are prepared by methods known in the art by introducing appropriate nucleotide changes into a native or variant TIE ligand homologue DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the TIE ligand homologues, the amino acid sequence variants of TIE are preferably constructed by mutating the DNA, either to arrive at an allele or an amino acid sequence variant that does not occur in nature.

One group of the mutations will be created within the domain or domains of the TIE ligand homologues of the present invention identified as being involved in the interaction with a TIE receptor, e.g. TIE-1 or TIE-2.

Alternatively or in addition, amino acid alterations can be made at sites that differ in TIE ligand homologues from various species, or in highly conserved regions, depending on the goal to be achieved.

Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1–3.

One helpful technique is called "alanine scanning" (Cunningham and Wells, *Science* 244, 1081–1085 [1989]). Here, a residue or group of target residues is identified and substituted by alanine or polyalanine. Those domains demonstrating functional sensitivity to the alanine substitutions are then refined by introducing further or other substituents at or for the sites of alanine substitution.

After identifying the desired mutation(s), the gene encoding an amino acid sequence variant of a TIE ligand homologue can, for example, be obtained by chemical synthesis as hereinabove described.

More preferably, DNA encoding a TIE ligand homologue amino acid sequence variant is prepared by site-directed mutagenesis of DNA that encodes an earlier prepared variant or a nonvariant version of the ligand. Site-directed (site-specific) mutagenesis allows the production of ligand variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al., *DNA* 2, 183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton, ed., Elsevier, Amsterdam (1981). This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M., *Nucleic Acids Res.* 10, 6487–6500 [1982]). Also, plasmid vectors that contain a single-stranded phage origin of replication (Veira et al., *Meth. Enzymol.* 153, 3 [1987]) may be employed to obtain single-stranded DNA. Alternatively, nucleotide substitutions are introduced by synthesizing the appropriate DNA fragment in vitro, and amplifying it by PCR procedures known in the art.

In general, site-specific mutagenesis herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. USA* 75, 5765 (1978). This primer is then annealed with the single-stranded protein sequence-containing vector, and subjected to DNA-polymerizing enzymes such as, *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate host cells such as JP101 cells, and clones are selected that include recombinant vectors bearing the mutated sequence arrangement. Thereafter, the mutated region may be removed and placed in an appropriate expression vector for protein production.

The PCR technique may also be used in creating amino acid sequence variants of a TIE ligand homologue. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

In a specific example of PCR mutagenesis, template plasmid DNA (1 µg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp$^R$ kits (obtained from Perkin-Elmer Cetus, Norwalk, Conn. and Emeryville, Calif.), and 25 pmole of each oligonucleotide primer, to a final volume of 50 µl. The reaction mixture is overlayered with 35 µl mineral oil. The reaction is denatured for 5 minutes at 100° C., placed briefly on ice, and then 1 µl Thermus aguaticus (Taq) DNA polymerase (5 units/1), purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C., 30 sec. 72° C., then 19 cycles of the following:

30 sec. 94° C., 30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to appropriate treatments for insertion into a vector.

Another method for preparing variants, cassette mutagenesis, is based on the technique described by Wells et al. [*Gene* 34, 315 (1985)]. The starting material is the plasmid (or vector) comprising the TIE ligand DNA to be mutated. The codon(s) within the TIE ligand to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA encoding the TIE ligand. After the restriction sites have been introduced into the plasmid, the plasmid is cut at these sites to linearize it. A double-stranded oligonucleotide encoding the sequence of the DNA between the restriction site but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated TIE ligand DNA sequence.

Additionally, the so-called phagemid display method may be useful in making amino acid sequence variants of native or variant TIE ligand homologues. This method involves (a) constructing a replicable expression vector comprising a first gene encoding an receptor to be mutated, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a suitable antigen so that at least a portion of the phagemid particles bind to the antigen; and (g) separating the phagemid particles that bind from those that do not. Steps (d) through (g) can be repeated one or more times. Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%. Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Also, normally the method will employ a helper phage selected from M13K07, M13R408, M13-VCS, and Phi X 174. The preferred helper phage is M13K07, and the preferred coat protein is the M13 Phage gene III coat protein. The preferred host is *E. coli*, and protease-deficient strains of *E. coli*.

Further details of the foregoing and similar mutagenesis techniques are found in general textbooks, such as, for example, Sambrook et al., *Molecular Cloning: A laboratory Manual* (New York: Cold Spring Harbor Laboratory Press, 1989), and *Current Protocols in Molecular Biology*, Ausubel et al., eds., Wiley-Interscience, 1991.

"Immunoadhesins" are chimeras which are traditionally constructed from a receptor sequence linked to an appropriate immunoglobulin constant domain sequence (immunoadhesins). Such structures are well known in the art. Immunoadhesins reported in the literature include fusions of the T cell receptor* [Gascoigne et al., *Proc. Natl.Acad. Sci. USA* 84, 2936–2940 (1987)]; CD4* [Capon et al., *Nature* 337, 525–531 (1989); Traunecker et al., *Nature*

339, 68–70 (1989); Zettmeissl et al., *DNA Cell Biol. USA* 9, 347–353 (1990); Byrn et al., *Nature* 344, 667–670 (1990)]; L-selectin (homing receptor) [Watson et al., *J. Cell. Biol.* 110, 2221–2229 (1990); Watson et al., *Nature* 349, 164–167 (1991)]; CD44* [Aruffo et al., *Cell* 61, 1303–1313 (1990)]; CD28* and B7* [Linsley et al., *J. Exp. Med.* 173, 721–730 (1991)]; CTLA4* [Lisley et al., *J. Exp. Med.* 174, 561–569 (1991)]; CD22* [Stamenkovic et al., *Cell* 66. 1133–1144 (1991)]; TNF receptor [Ashkenazi et al., *Proc. Natl. Acad. Sci. USA* 88, 10535–10539 (1991); Lesslauer et al., *Eur. J. Immunol.* 27, 2883–2886 (1991); Peppel et al., *J. Exp. Med.* 174, 1483–1489 (1991)]; NP receptors [Bennett et al., *J. Biol. Chem.* 266, 23060–23067 (1991)]; IgE receptor α-chain* [Ridgway and Gorman, *J. Cell. Biol.* 115, abstr. 1448 (1991)]; HGF receptor [Mark, M. R. et al., 1992, *J. Biol. Chem.* submitted], where the asterisk (*) indicates that the receptor is member of the immunoglobuhn superfamily.

Ligand-immunoglobulin chimeras are also known, and are disclosed, for example, in U.S. Pat. No. 5,304,640 (for L-selectin ligands); U.S. Pat. Nos. 5,316,921 and 5,328,837 (for HGF variants). These chimeras can be made in a similar way to the construction of receptor-immunoglobulin chimeras.

Covalent modifications of the TIE ligand homologues of the present invention are included within the scope herein. Such modifications are traditionally introduced by reacting targeted amino acid residues of the TIE ligand with an organic derivatizing agent that is capable of reacting with selected sides or terminal residues, or by harnessing mechanisms of post-translational modifications that function in selected recombinant host cells. The resultant covalent derivatives are useful in programs directed at identifying residues important for biological activity, for immunoassays, or for the preparation of anti-TIE ligand antibodies for immunoaffinity purification of the recombinant. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R'—N=C=N—R') such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl, threonyl or tyrosyl residues, methylation of the α-amino groups of lysine, arginine, and histidine side chains (T. E. Creighton, *Proteins: Structure and Molecular Properties,* W. H. Freeman & Co., San Francisco, pp. 79–86 [1983]), acetylation of the N-terminal amine, and amidation of any C-terminal carboxyl group. The molecules may further be covalently linked to nonproteinaceous polymers, e.g. polyethylene glycol, polypropylene glycol or polyoxyalkylenes, in the manner set forth in U.S. Ser. No. 07/275,296 or U.S. Pat. Nos. 4,640,835; 4,496,689; 4,301,144; 4,670,417; 4,791,192 or 4,179,337.

Derivatization with bifunctional agents is useful for preparing intramolecular aggregates of the TIE ligand with polypeptides as well as for cross-linking the TIE ligand polypeptide to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio] propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

Other derivatives comprise the novel peptides of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The TIE ligands may be linked to various nonproteinaceous polymers, such as polyethylene glycol (PEG), polypropylene glycol or polyoxyalkylenes, in the manner set forth in U.S. Pat. Nos. 4,640,835; 4,496,689; 4,301,144; 4,670,417; 4,791,192 or 4,179,337. These variants, just as the immunoadhesins of the present invention are expected to have longer half-lives than the corresponding native TIE ligand homologues.

The TIE ligand homologues may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remington's Pharmaceutical Sciences*, 16th Edition, Osol, A., Ed. (1980).

The term "native TIE receptor" is used herein to refer to a TIE receptor of any animal species, including, but not limited to, humans, other higher primates, e.g. monkeys, and rodents, e.g. rats and mice. The definition specifically includes the TIE-2 receptor, disclosed, for example, in PCT application Ser. No. WO 95/13387 (published May 18, 1995), and the endothelial cell receptor tyrosine kinase termed "TIE" in PCT Application Publication No. WO 93/14124 (published Jul. 22, 1993), and preferably is TIE-2.

B. ANTI-TIE LIGAND ANTIBODIES

The present invention covers agonist and antagonist antibodies, specifically binding the TIE ligand homologues. The antibodies may be monoclonal or polyclonal, and include, without limitation, mature antibodies, antibody fragments (e.g. Fab, F(ab')$_2$, F$_v$, etc.), single-chain antibodies and various chain combinations.

The term "antibody" is used in the broadest sense and specifically covers single monoclonal antibodies (including agonist, antagonist, and neutralizing antibodies) specifically binding a TIE ligand of the present invention and antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-TIE ligand antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. See, e.g. U.S. Pat. No. 4,816,567 and Mage et al., in *Monoclonal Antibody Production Techniques and Applications*, pp.79–97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256:495 (1975), or may be made by recombinant DNA methods such as described in U.S. Pat. No. 4,816,567. The "monoclonal antibodies" may also be isolated from phage libraries generated using the techniques described in McCafferty et al., *Nature*, 348:552–554 (1990), for example.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

Polyclonal antibodies to a TIE ligand homologue of the present invention generally are raised in animals by multiple subcutaneous (sc) or intraperitoneal (ip) injections of the TIE ligand homologues and an adjuvant. It may be useful to conjugate the TIE ligand homologues or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, SOCl$_2$, or R$^1$N=C=NR, where R and R$^1$ are different alkyl groups.

Animals are immunized against the immunogenic conjugates or derivatives by combining 1 mg or 1 μg of conjugate (for rabbits or mice, respectively) with 3 volumes of Freud's complete adjuvant and injecting the solution intradermally at multiple sites. One month later the animals are boosted with ⅕ to ¹⁄₁₀ the original amount of conjugate in Freud's complete adjuvant by subcutaneous injection at multiple sites. 7 to 14 days later the animals are bled and the serum is assayed for anti-TIE ligand antibody titer. Animals are boosted until the titer plateaus. Preferably, the animal boosted with the conjugate of the same TIE ligand, but conjugated to a different protein and/or through a different cross-linking reagent. Conjugates also can be made in recombinant cell culture as protein fusions. Also, aggregating agents such as alum are used to enhance the immune response.

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-TIE ligand monoclonal antibodies of the invention may be made using the hybridoma method first described by Kohler & Milstein, Nature 256:495 (1975), or may be made by recombinant DNA methods [Cabilly, et al., U.S. Pat. No. 4,816,567].

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell [Goding, *Monoclonal Antibodies: Principles and Practice*, pp.59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies [Kozbor, J. Immunol. 133:3001 (1984); Brodeur, et al., *Monoclonal Antibody Production Techniques and Applications*, pp.51–63 (Marcel Dekker, Inc., New York, 1987)].

Culture medium in which hybridoma cells are growing is assayed for production of monoclonal antibodies directed against the TIE ligand homologues. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, Anal. Biochem. 107:220 (1980).

After hybridoma cells are identified that produce antibodies of the desired specificity, affinity, and/or activity, the clones may be subcloned by limiting dilution procedures and grown by standard methods. Goding, *Monoclonal Antibodies: Principles and Practice*, pp.59–104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-TIE ligand monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a TIE ligand homologues of the present invention and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or 125I, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by Hunter, et al., *Nature* 144:945 (1962); David, et al., *Biochemistry* 13:1014 (1974); Pain, et al., *J. Immunol. Meth.* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc., 1987).

Competitive binding assays rely on the ability of a labeled standard (which may be a TIE ligand homologue or an immunologically reactive portion thereof) to compete with the test sample analyte (TIE ligand homologues) for binding with a limited amount of antibody. The amount of TIE ligand homologues in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376, 110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature* 321, 522–525 (1986); Riechmann et al., *Nature* 332, 323–327 (1988); Verhoeyen et al., *Science* 239, 1534–1536 (1988)], by substituting rodent CDRs or CDR sequences for the corresponding sequences of a human antibody. Accordingly, such "humanized" antibodies are chimeric antibodies (Cabilly, supra, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551–255 (1993); Jakobovits et al., *Nature* 362, 255–258 (1993).

Bispecific antibodies are monoclonal, preferably human or humanized, antibodies that have binding specificities for at least two different antigens. In the present case, one of the binding specificities is for a particular TIE ligand homologue, the other one is for any other antigen, and preferably for another ligand. For example, bispecific antibodies specifically binding two different TIE ligand homologue are within the scope of the present invention.

Methods for making bispecific antibodies are known in the art.

Traditionally, the recombinant production of bispecific antibodies is based on the coexpression of two immunoglobulin heavy chain-light chain pairs, where the two heavy chains have different specificities (Millstein and Cuello, *Nature* 305, 537–539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al., *EMBO* 10 3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, and second and third constant regions of an immunoglobulin heavy chain (CH2 and CH3). It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed Aug.17, 1992.

For further details of generating bispecific antibodies see, for example, Suresh et al., *Methods in Enzymology* 121, 210 (1986).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

The term "agonist" is used to refer to peptide and non-peptide analogs of the native TIE ligand homologues of the present invention and to antibodies specifically binding such native TIE ligands, provided that they have the ability to signal through a native TIE receptor (e.g. TIE-2). In other words, the term "agonist" is defined in the context of the biological role of the TIE receptor, and not in relation to the biological role of a native TIE ligand homologue, which, as noted before, may be an agonist or antagonist of the TIE receptor biological function. Preferred agonists are promoters of vascularization.

The term "antagonist" is used to refer to peptide and non-peptide analogs of the native TIE ligand homologues of the present invention and to antibodies specifically binding such native TIE ligand homologues, provided that they have the ability to inhibit the biological function of a native TIE receptor (e.g. TIE-2). Again, the term "antagonist" is defined in the context of the biological role of the TIE receptor, and not in relation to the biological activity of a native TIE ligand homologue, which may be either an agonist or an antagonist of the TIE receptor biological function. Preferred antagonists are inhibitors of vasculogenesis.

C. CLONING AND EXPRESSION OF THE TIE LIGAND HOMOLOGUES

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA of expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, the signal sequence may be a component of the vector, or it may be a part of the TIE ligand molecule that is inserted into the vector. If the signal sequence is heterologous, it should be selected such that it is recognized and processed (i.e. cleaved by a signal peptidase) by the host cell.

Heterologous signal sequences suitable for prokaryotic host cells are preferably prokaryotic signal sequences, such as the α-amylase, ompA, ompC, ompE, ompF, alkaline phosphatase, penicillinase, lpp, or heat-stable enterotoxin II leaders. For yeast secretion the yeast invertase, amylase, alpha factor, or acid phosphatase leaders may, for example, be used. In mammalian cell expression mammalian signal sequences are most suitable. The listed signal sequences are for illustration only, and do not limit the scope of the present invention in any way.

(ii) Origin of Replication Component

Both expression and cloning vectors contain a nucleic acid sequence that enabled the vector to replicate in one or more selected host cells. Generally, in cloning vectors this sequence is one that enables the vector to replicate independently of the host chromosomes, and includes origins of replication or autonomously replicating sequences. Such sequence are well known for a variety of bacteria, yeast and viruses. The origin of replication from the well-known plasmid pBR322 is suitable for most gram negative bacteria, the 2 μplasmid origin for yeast and various viral origins (SV40, polyoma, adenovirus, VSV or BPV) are useful for cloning vectors in mammalian cells. Origins of replication are not needed for mammalian expression vectors (the SV40 origin may typically be used only because it contains the early promoter). Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA is also cloned by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the DNA encoding the desired heterologous polypeptide. However, the recovery of genomic DNA is more complex than that of an exogenously replicated vector because restriction enzyme digestion is required to excise the encoded polypeptide molecule.

(iii) Selection Gene Component

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies, or (c) supply critical nutrients not available from complex media, e.g. the gene encoding D-alanine racemase for bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin [Southern et al., *J. Molec. Appl. Genet.* 1, 327 (1982)], mycophenolic acid [Mulligan et al., *Science* 209, 1422 (1980)], or hygromycin [Sudgen et al., *Mol. Cel. Biol.* 5, 410–413 (1985)]. The three examples given above employ bacterial genes under eukaryotic control to convey resistance to the appropriate drug G418 or neomycin (geneticin), xgpt (mycophenolic acid), or hygromycin, respectively.

Other examples of suitable selectable markers for mammalian cells are dihydrofolate reductase (DHFR) or thyrnidine kinase. Such markers enable the identification of cells which were competent to take up the desired nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the desired polypeptide. Amplification is the process by which genes in greater demand for the production of a protein critical for growth are reiterated in tandem within the chromosomes of successive generations of recombinant cells. Increased quantities of the desired polypeptide are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Nat'l. Acad. Sci. USA* 77, 4216 (1980). A particularly useful DHFR is a mutant DHFR that is highly resistant to MTX (EP 117,060). This selection agent can be used with any otherwise suitable host, e.g. ATCC No. CCL61 CHO-K1, notwithstanding the presence of endogenous DHFR. The DNA encoding DHFR and the desired polypeptide, respectively, then is amplified by exposure to an agent (methotrexate, or MTX) that inactivates the DHFR. One ensures that the cell requires more DHFR (and consequently amplifies all exogenous DNA) by selecting only for cells that can grow in successive rounds of ever-greater MTX concentration. Alternatively, hosts co-transformed with genes encoding the desired polypeptide, wild-type DHFR, and another selectable marker such as the neo gene can be identified using a selection agent for the selectable marker such as G418 and then selected and amplified using methotrexate in a wild-type host that contains endogenous DHFR. (See also U.S. Pat. No. 4,965,199).

A suitable selection gene for use in yeast is the trp1 gene present in the yeast plasmid YRp7 (Stinchcomb et al., 1979, *Nature* 282:39; Kingsman et al., 1979, *Gene* 7:141; or Tschemper et al., 1980, *Gene* 10: 157). The trp1 gene provides a selection marker for a mutant strain of yeast lacking the ability to grow in tryptophan, for example, ATCC No. 44076 or PEP4-1 (Jones, 1977, *Genetics* 85:12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

(iv) Promoter Component

Expression vectors, unlike cloning vectors, should contain a promoter which is recognized by the host organism and is operably linked to the nucleic acid encoding the desired polypeptide. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the desired polypeptide by removing them from their gene of origin by restriction enzyme digestion, followed by insertion 5' to the start codon for the polypeptide to be expressed. This is not to say that the genomic promoter for a TIE ligand is not usable. However, heterologous promoters generally will result in greater transcription and higher yields of expressed TIE ligands as compared to the native TIE ligand promoters.

Promoters suitable for use with prokaryotic hosts include the β-lactamase and lactose promoter systems (Chang et al., *Nature* 275:615 (1978); and Goeddel et al., *Nature* 281:544 (1979)), alkaline phosphatase, a tryptophan (trp) promoter system (Goeddel, *Nucleic Acids Res.* 8:4057 (1980) and EPO Appln. Publ. No. 36,776) and hybrid promoters such as the tac promoter (H. de Boer et al., *Proc. Nat'l. Acad. Sci. USA* 80:21–25 (1983)). However, other known bacterial promoters are suitable. Their nucleotide sequences have been published, thereby enabling a skilled worker operably to ligate them to DNA encoding a TIE ligand (Siebenlist et al., *Cell* 20:269 (1980)) using linkers or adaptors to supply any required restriction sites. Promoters for use in bacterial systems also will contain a Shine-Dalgarno (S.D.) sequence operably linked to the DNA encoding a TIE ligand.

Suitable promoting sequences for use with yeast hosts include the promoters for 3-phosphoglycerate kinase (Hitzeman et a., *J. Biol. Chem.* 255:2073 (1980)) or other glycolytic enzymes (Hess et al., *J. Adv. Enzyme Reg.* 7:149 (1978); and Holland, *Biochemistry* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

TIE ligand homologue transcription from vectors in mammalian host cells may be controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat shock promoters, and from the promoter normally associated with the TIE ligand homologue sequence, provided such promoters are compatible with the host cell systems.

The early and late promoters of the SV40 virus are conveniently obtained as an SV40 restriction fragment which also contains the SV40 viral origin of replication [Fiers et al., Nature 273:113 (1978), Mulligan and Berg, Science 209, 1422–1427 (1980); Pavlakis et al., Proc. Natl. Acad. Sci. USA 78, 7398–7402 (1981)]. The immediate early promoter of the human cytomegalovirus is conveniently obtained as a HindIII E restriction fragment [Greenaway et al., Gene 18,355–360(1982)]. A system for expressing DNA in mammalian hosts using the bovine papilloma virus as a vector is disclosed in U.S. Pat. No. 4,419,446. A modification of this system is described in U.S. Pat. No. 4,601,978. See also, Gray et al., Nature 295, 503–508 (1982) on expressing cDNA encoding human immune interferon in monkey cells; Reyes et al., Nature 297, 598–601 (1982) on expressing human β-interferon cDNA in mouse cells under the control of a thymidine kinase promoter from herpes simplex virus; Canaani and Berg, Proc. Natl. Acad. Sci. USA 79, 5166–5170 (1982) on expression of the human interferon β1 gene in cultured mouse and rabbit cells; and Gorman et al., Proc. Natl. Acad. Sci., USA 79, 6777–6781 (1982) on expression of bacterial CAT sequences in CV-1 monkey kidney cells, chicken embryo fibroblasts, Chinese hamster ovary cells, HeLa cells, and mouse HIN-3T3 cells using the Rous sarcoma virus long terminal repeat as a promoter.

(v) Enhancer Element Component

Transcription of a DNA encoding the TIE ligand homologues of the present invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent having been found 5' [Laimins et al., Proc. Natl. Acad. Sci. USA 78, 993 (1981)] and 3' [Lasky et al., Mol Cel. Biol. 3, 1108 (1983)] to the transcription unit, within an intron [Banerji et al., Cell 33, 729 (1983)] as well as within the coding sequence itself [Osborne et al., Mol. Cel. Biol. 4 1293 (1984)]. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, Nature 297, 17–18 (1982) on enhancing elements for activation of eukaryotic promoters. The enhancer may be spliced into the vector at a position 5' or 3' to the TIE ligand homologue DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the TIE ligand homologue. The 3' untranslated regions also include transcription termination sites.

Construction of suitable vectors containing one or more of the above listed components, the desired coding and control sequences, employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform E. coli K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., Nucleic Acids Res. 9, 309 (1981) or by the method of Maxam et al., Methods in Enzymology 65, 499 (1980).

Particularly useful in the practice of this invention are expression vectors that provide for the transient expression in mammalian cells of DNA encoding a TIE ligand homologue. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient systems, comprising a suitable expression vector and a host cell, allow for the convenient positive identification of polypeptides encoded by clones DNAs, as well as for the rapid screening of such polypeptides for desired biological or physiological properties. Thus, transient expression systems are particularly useful in the invention for purposes of identifying analogs and variants of a TIE ligand homologue.

Other methods, vectors, and host cells suitable for adaptation to the synthesis of the TIE polypeptides in recombinant vertebrate cell culture are described in Getting et al., Nature 293, 620–625 (1981); Mantel et al., Nature 281, 40–46 (1979); Levinson et al.; EP 117,060 and EP 117,058. A particularly useful plasmid for mammalian cell culture expression of the TIE ligand homologue polypeptides is pRK5 (EP 307,247), along with its derivatives, such as, pRK5D that has an sp6 transcription initiation site followed by an SfiI restriction enzyme site preceding the Xho/NotII cDNA cloning sites, and pRK5B, a precursor of pRK5D that does not contain the SfiI site; see, Holmes et al., *Science* 253, 1278–1280 (1991).

(vii) Construction and analysis of vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequences by the methods of Messing et al., *Nuclei Acids Res.* 9, 309 (1981) or by the method of Maxam et al., *Methods in Enzymology* 65, 499 (1980).

(viii) Transient expression vectors

Particularly useful in the practice of this invention are expression vectors that provide for the transient expression in mammalian cells of DNA encoding a TIE ligand homologue. In general, transient expression involves the use of an expression vector that is able to replicate efficiently in a host cell, such that the host cell accumulates many copies of the expression vector and, in turn, synthesizes high level of a desired polypeptide encoded by the expression vector. Sambrook et al., supra, pp. 16.17–16.22. Transient expression systems, comprising a suitable expression vector and a host cell, allow for the convenient positive screening of such polypeptides for desired biological or physiological properties. Thus transient expression systems are particularly useful in the invention for purposes of identifying analogs and variants of native TIE ligand homologues with the requisite biological activity.

(ix) Suitable exemplary vertebrate cell vectors

Other methods, vectors, and host cells suitable for adaptation to the synthesis of a TIE ligand homologue (including functional derivatives of native proteins) in recombinant vertebrate cell culture are described in Gething et al., *Nature* 293, 620–625 (1981); Mantei et al., *Nature* 281, 40–46 (1979); Levinson et al., EP 117,060; and EP 117,058. A particularly useful plasmid for mammalian cell culture expression of a TIE ligand is pRK5 (EP 307,247) or pSVI6B (PCT Publication No. WO 91/08291).

Suitable host cells for cloning or expressing the vectors herein are the prokaryote, yeast or higher eukaryote cells described above. Suitable prokaryotes include gram negative or gram positive organisms, for example *E. coli* or bacilli. A preferred cloning host is *E. coli* 294 (ATCC 31,446) although other gram negative or gram positive prokaryotes such as *E coli* B, *E. coli* X1776 (ATCC 31,537), *E. coli* W3110 (ATCC 27,325), Pseudomonas species, or *Serratia Marcesans* are suitable.

In addition to prokaryotes, eukaryotic microbes such as filamentous fungi or yeast are suitable hosts for vectors herein. *Saccharomyces cerevisiae,* or common baker's yeast, is the most commonly used among lower eukaryotic host microorganisms. However, a number of other genera, species and strains are commonly available and useful herein, such as *S. pombe* [Beach and Nurse, *Nature* 290, 140 (1981)], *Kluyveromyces lactis* [Louvencourt et al., *J. Bacteriol.* 737 (1983)]; *yarrowia* (EP 402,226); *Pichia pastoris* (EP 183,070), *Trichoderma reesia* (EP 244,234), *Neurospora crassa* [Case et al., *Proc. Natl. Acad. Sci. USA* 76, 5259–5263 (1979)]; and Aspergillus hosts such as *A. nidulans* [Ballance et al., *Biochem. Biophys. Res. Commun.* 112, 284–289 (1983); Tilburn et al., *Gene* 26, 205–221 (1983); Yelton et al., *Proc. Natl. Acad. Sci. USA* 81, 1470–1474 (1984)] and *A. niger* [Kelly and Hynes, *EMBO J.* 4, 475–479 (1985)].

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plants and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melangaster* (fruitfly), and *Bombyx mori* host cells have been identified. See, e.g. Luckow et al., *Bio/Technology* 6, 47–55 (1988); Miller et al., in *Genetic Engineering,* Setlow, J. K. et al., eds., Vol. 8 (Plenum Publishing, 1986), pp. 277–279; and Maeda et al., *Nature* 315, 592–594 (1985). A variety of such viral strains are publicly available, e.g. the L-1 variant of *Autographa californica* NPV, and such viruses may be used as the virus herein according to the present invention, particularly for transfection of *Spodoptera frugiperda* cells.

Generally, plant cells are transfected by incubation with certain strains of the bacterium *Agrobacterium tumefaciens,* which has been previously manipulated to contain the TIE ligand homologue DNA. During incubation of the plant cell culture with *A. tumefaciens,* the DNA encoding a TIE ligand homologue is transferred to the plant cell host such that it is transfected, and will, under appropriate conditions, express the TIE ligand homologue DNA. In addition, regulatory and signal sequences compatible with plant cells are available, such as the nopaline synthase promoter and polyadenylation signal sequences. Depicker et al., *J. Mol. Appl. Gen.* 1, 561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

However, interest has been greatest in vertebrate cells, and propagation of vertebrate cells in culture (tissue culture) is per se well known. See *Tissue Culture,* Academic Press, Kruse and Patterson, editors (1973). Examples of useful mammalian host cell lines are monkey kidney CV1 line transformed by SV40 (COS-7, ATCC CRL 1651); human embryonic kidney cell line [293 or 293 cells subcloned for growth in suspension culture, Graham et al., *J. Gen. Virol.* 36, 59 (1977)]; baby hamster kidney cells 9BHK, ATCC CCL 10); Chinese hamster ovary cells/-DHFR [CHO, Urlaub and Chasin, *Proc. Natl. Acad. Sci. USA* 77, 4216 (1980)]; mouse sertolli cells [TM4, Mather, *Biol. Reprod.* 23, 243–251 (1980)]; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 8065); mouse mammary tumor (MMT 060562, ATCC CCL51); TRI cells [Mather et al., *Annals N.Y. Acad. Sci.* 383, 44068 (1982)]; MRC 5 cells; FS4 cells; and a human hepatoma cell line (Hep G2). Preferred host cells are human embryonic kidney 293 and Chinese hamster ovary cells.

Particularly preferred host cells for the purpose of the present invention are vertebrate cells producing the TIE ligand homologues of the present invention.

Host cells are transfected and preferably transformed with the above-described expression or cloning vectors and cultured in conventional nutrient media modified as is appropriate for inducing promoters or selecting transformants containing amplified genes.

Prokaryotes cells used to produced the TIE ligand homologues of this invention are cultured in suitable media as describe generally in Sambrook et al., supra.

Mammalian cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham and Wallace, *Meth. Enzymol.* 58, 44 (1979); Barnes and Sato, *Anal. Biochem.* 102, 255 (1980), U.S. Pat Nos. 4,767,704; 4,657,866; 4,927,762; or 4,560,655; WO 90/03430; WO 87/00195 or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug) trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, suitably are those previously used with the host cell selected for cloning or expression, as the case may be, and will be apparent to the ordinary artisan.

The host cells referred to in this disclosure encompass cells in in vitro cell culture as well as cells that are within a host animal or plant.

It is further envisioned that the TIE ligand homologues of this invention may be produced by homologous recombination, or with recombinant production methods utilizing control elements introduced into cells already containing DNA encoding the particular TIE ligand homologue.

Gene amplification and/or expression may be measured in a sample directly, for example, by conventional Southern blotting, Northern blotting to quantitate the transcription of mRNA [Thomas, *Proc. Natl. Acad. Sci. USA* 77, 5201–5205 (1980)], dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as a site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to the surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With inmmunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hse et al., *Am. J. Clin. Pharm.* 75, 734–738 (1980).

Antibodies useful for immunohistochemical staining and/or assay of sample fluids may be either monoclonal or polyclonal, and may be prepared in any animal. Conveniently, the antibodies may be prepared against a native TIE ligand homologue polypeptide of the present invention, or against a synthetic peptide based on the DNA sequence provided herein as described further hereinbelow.

The TIE ligand homologue may be produced in host cells in the form of inclusion bodies or secreted into the periplasmic space or the culture medium, and is typically recovered from host cell lysates. The recombinant ligands may be purified by any technique allowing for the subsequent formation of a stable protein.

When the TIE ligand homologue is expressed in a recombinant cell other than one of human origin, it is completely free of proteins or polypeptides of human origin. However, it is necessary to purify the TEE ligand homologue from recombinant cell proteins or polypeptides to obtain preparations that are substantially homogenous as to the ligand. As a first step, the culture medium or lysate is centrifuged to remove particulate cell debris. The membrane and soluble protein fractions are then separated. The TIE ligand homologue may then be purified from the soluble protein fraction. The following procedures are exemplary of suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; and protein A Sepharose columns to remove contaminants such as IgG.

Functional derivatives of the TIE ligand homologues in which residues have been deleted, inserted and/or substituted are recovered in the same fashion as the native ligands, taking into account of any substantial changes in properties occasioned by the alteration. For example, fusion of the TIE ligand homologue with another protein or polypeptide, e.g. a bacterial or viral antigen, facilitates purification; an immunoaffinity column containing antibody to the antigen can be used to absorb the fusion. Immunoaffinity columns such as a rabbit polyclonal anti-TIE ligand homologue column can be employed to absorb TIE ligand homologue variants by binding to at least one remaining immune epitope. A protease inhibitor, such as phenyl methyl sulfonyl fluoride (PMSF) also may be useful to inhibit proteolytic degradation during purification, and antibiotics may be included to prevent the growth of adventitious contaminants. The TIE ligand homologues of the present invention are conveniently purified by affinity chromatography, based upon their ability to bind to a TIE receptor, e.g. TIE-2.

One skilled in the art will appreciate that purification methods suitable for native TIE ligands may require modification to account for changes in the character of a native TIE ligand homologue or its variants upon expression in recombinant cell culture.

D. USE OF THE TIE LIGAND HOMOLOGUES, NUCLEIC ACID MOLECULES AND ANTIBODIES

The TIE ligand homologues of the present invention are useful in promoting the survival and/or growth and/or differentiation of TIE receptor (e.g. TIE-2 receptor) expressing cells in cell culture.

The TIE ligand homologues may be additionally used to identify cells which express native TIE receptors, e.g. the TIE-2 receptor. To this end, a detectably labeled ligand is contacted with a target cell under condition permitting its binding to the TIE receptor, and the binding is monitored.

The TIE ligand homologues herein may also be used to identify molecules exhibiting a biological activity of a TIE ligand homologue, for example, by exposing a cell expressing a TIE ligand homologue herein to a test molecule, and detecting the specific binding of the test molecule to a TIE (e.g. TIE-2) receptor, either by direct detection, or base upon secondary biological effects. This approach is particularly suitable for identifying new members of the TIE ligand family, or for screening peptide or non-peptide small molecule libraries.

The TIE ligand homologues disclosed herein are also useful in screening assays designed to identify agonists or antagonists of a native TIE (e.g. TIE-2) receptor that play an important role in bone development, maturation or growth, or in muscle growth or development and/or promote or inhibit angiogenesis. For example, antagonists of the TIE-2 receptor may be identified based upon their ability to block the binding of a TIE ligand homologue of the present invention to a native TIE receptor, as measured, for example, by using BiAcore biosensor technology (BIAcore; Pharmacia Biosensor, Midscataway, N.J.); or by monitoring their ability to block the biological response caused by a biologically active TIE ligand homologue herein. Biological responses that may be monitored include, for example, the phosphorylation of the TIE-2 receptor or downstream components of the TIE-2 signal transduction pathway, or survival, growth or differentiation of cells expressing the TIE-2 receptor. Cell-based assays, utilizing cells that do not normally the TIE-2 receptor, engineered to express this receptor, or to coexpress the TIE-2 receptor and a TIE ligand homologue of the present invention, are particularly convenient to use.

In a particular embodiment, small molecule agonists and antagonists of a native TIE receptor, e.g. the TIE-2 receptor, can be identified, based upon their ability to interfere with the TIE ligand/TIE receptor interaction. There are numerous ways for measuring the specific binding of a test molecule to a TIE receptor, including, but not limited to detecting or measuring the amount of a test molecule bound to the surface of intact cells expressing the TIE receptor, cross-linked to the TIE receptor in cell lysates, or bound to the TIE receptor in vitro.

Detectably labeled TIE ligand homologues include, for example, TIE ligand homologues covalently or non-covalently linked to a radioactive substances, e.g. $^{125}$I, a fluorescent substance, a substance having enzymatic activity (preferably suitable for colorimetric detection), a substrate for an enzyme (preferably suitable for colorimetric detection), or a substance that can be recognized by a(n) (detectably labeled) antibody molecule.

The assays of the present invention may be performed in a manner-similar to that described in PCT Publication WO 96/11269, published Apr. 18, 1996.

The TIE ligands of the present invention are also useful for purifying TIE receptors, e.g. TIE-2 receptors, optionally used in the form of immunoadhesins, in which the TIE ligand homologue or the TIE receptor binding portion thereof is fused to an immunoglobulin heavy or light chain constant region.

The nucleic acid molecules of the present invention are useful for detecting the expression of TIE ligands in cells or tissue sections. Cells or tissue sections may be contacted with a detectably labeled nucleic acid molecule encoding a TIE ligand homologue of the present invention under hybridizing conditions, and the presence of mRNA hybridized to the nucleic acid molecule determined, thereby detecting the expression of the TIE ligand homologue.

Antibodies of the present invention may, for example, be used in immunoassays to measure the amount of a TIE ligand homologue in a biological sample. The biological sample is contacted with an antibody or antibody mixture specifically binding the a TIE ligand homologue of the present invention, and the amount of the complex formed with a ligand present in the test sample is measured.

Antibodies to the TIE ligand homologues herein may additionally be used for the delivery of cytotoxic molecules, e.g. radioisotopes or toxins, or therapeutic agents to cells expressing a corresponding TIE receptor. The therapeutic agents may, for example, be other TIE ligands, including the TIE-2 ligand, members of the vascular endothelial growth factor (VEGF) family, or known anti-tumor agents, and agents known to be associated with muscle growth or development, or bone development, maturation, or growth.

Anti-TIE ligand homologues antibodies are also suitable as diagnostic agents, to detect disease states associated with the expression of a TIE (e.g. TIE-2) receptor. Thus, detectably labeled TIE ligand homologues and antibody agonists of a TIE receptor can be used for imaging the presence of angiogenesis.

In addition, the new TIE ligand homologues herein can be used to promote neovascularization, and may be useful for inhibiting tumor growth.

Further potential therapeutic uses include the modulation of muscle and bone development, maturation, or growth.

For therapeutic use, the TIE ligand homologues or anti-TIE ligand homologues antibodies of the present invention are formulated as therapeutic composition comprising the active ingredient(s) in admixture with a pharmacologically acceptable vehicle, suitable for systemic or topical application. The pharmaceutical compositions of the present invention are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules) or in macroemulsions. Such techniques are disclosed in *Remington's Pharmaceutical Sciences,* supra.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Suitable examples of sustained release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (U. Sidman et al., 1983, "Biopolymers" 22 (1): 547–556), poly (2-hydroxyethyl-methacrylate) (R. Langer, et al., 1981, "J. Biomed. Mater. Res." 15: 167–277 and R. Langer, 1982, Chem. Tech." 12: 98–105), ethylene vinyl acetate (R. Langer et al., Id.) or poly-D-(−)-3-hydroxybutyric acid (EP 133, 988A). Sustained release compositions also include liposomes. Liposomes containing a molecule within the scope of the present invention are prepared by methods known per se: DE 3,218,121A; Epstein et al., 1985, "Proc. Natl. Acad. Sci. USA" 82: 3688–3692; Hwang et al., 1980, "Proc. Natl. Acad. Sci. USA" 77: 4030–4034; EP 52322A; EP 36676A; EP 88046A; EP 143949A; EP 142641A; Japanese patent application 83-118008; U.S. Pat. Nos. 4,485,045 and 4,544, 545; and EP 102,324A. Ordinarily the liposomes are of the small (about 200–800 Angstroms) unilamelar type in which the lipid content is greater than about 30 mol. % cholesterol, the selected proportion being adjusted for the optimal NT-4 therapy.

An effective amount of a molecule of the present invention to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 $\mu$g/kg to up to 100 mg/kg or more, depending on the factors mentioned above. Typically, the clinician will administer a molecule of the present invention until a dosage is reached that provides the required biological effect. The progress of this therapy is easily monitored by conventional assays.

Further details of the invention will be apparent from the following non-limiting examples.

Reference Example 1
Identification of the FLS 139 Ligand

FLS139 was identified in a cDNA library prepared from human fetal liver mRNA obtained from Clontech Laboratories, Inc. Palo Alto, Calif. USA, catalog no. 64018-1, following the protocol described in "Instruction Manual: Superscript® Lambda System for cDNA Synthesis and λ cloning," cat. No. 19643-014, Life Technologies, Gaithersburg, Md., USA which is herein incorporated by reference. Unless otherwise noted, all reagents were also obtained from Life Technologies. The overall procedure can be summarized into the following steps: (1) First strand synthesis; (2) Second strand synthesis; (3) Adaptor addition; (4) Enzymatic digestion; (5) Gel isolation of cDNA; (6) Ligation into vector; and (7) Transformation.

First Strand Synthesis

Not1 primer-adapter (Life Tech., 2 $\mu$l, 0.5 $\mu$g/$\mu$l) was added to a sterile 1.5 ml microcentrifuge tube to which was added poly A+mRNA (7 $\mu$l, 5 $\mu$g). The reaction tube was heated to 70° C. for 5 minutes or time sufficient to denature the secondary structure of the mRNA. The reaction was then chilled on ice and 5×First strand buffer (Life Tech., 4 $\mu$l), 0.1 M DTT (2 $\mu$l) and 10 mM DNTP Mix (Life Tech., 1 $\mu$l) were added and then heated to 37° C. for 2 minutes to equilibrate the temperature. Superscript II® reverse transcriptase (Life Tech., 5 $\mu$l) was then added, the reaction tube mixed well and incubated at 37° C. for 1 hour, and terminated by placement on ice. The final concentration of the reactants was the following: 50 MM Tris-HCl (pH 8.3); 75 mM KCl; 3 mM MgCl$_2$; 10 mM DTT; 500 $\mu$M each dATP, dCTP, dGTP and dTTP; 50 $\mu$g/ml Not 1 primer-adapter; 5 $\mu$g (250 $\mu$g/ml) mRNA; 50,000 U/ml Superscript II® reverse transcriptase.

Second Strand Synthesis

While on ice, the following reagents were added to the reaction tube from the first strand synthesis, the reaction well mixed and allowed to react at 16° C. for 2 hours, taking care not to allow the temperature to go above 16° C.: distilled water (93 $\mu$l); 5×Second strand buffer (30 $\mu$l ); dNTP mix (3 $\mu$l); 10 U/$\mu$l E. Coli DNA ligase (1 $\mu$l); 10 U/$\mu$l E. Coli DNA polymerase I (4 $\mu$l); 2 U/$\mu$l E. Coli RNase H (1 $\mu$l). 10 U T4 DNA Polymerase (2 $\mu$l) was added and the reaction continued to incubate at 16° C. for another 5 minutes. The final concentration of the reaction was the following: 25 mM Tris-HCl (pH 7.5); 100 mM KCl; 5 mM MgCl$_2$; 10 mM (NH$_4$)$_2$SO$_4$; 0.15 mM β-NAD+; 250 $\mu$M each dATP, dCTP, dGTP, dTTP; 1.2 mM DTT; 65 U/ml DNA ligase; 250 U/ml DNA polymerase I; 13 U/ml Rnase H. The reaction has halted by placement on ice and by addition of 0.5 M EDTA (10 $\mu$l), then extracted through phenol:chloroform:isoamyl alcohol (25:24:1, 150 $\mu$l). The aqueous phase was removed, collected and diluted into 5M NaCl (15 $\mu$l) and absolute ethanol (−20° C., 400 $\mu$l) and centrifuged for 2 minutes at 14,000×g. The supernatant was carefully removed from the resulting DNA pellet, the pellet resuspended in 70% ethanol (0.5 ml) and centrifuged again for 2 minutes at 14,000×g. The supernatant was again removed and the pellet dried in a speedvac.

Adapter Addition

The following reagents were added to the cDNA pellet from the Second strand synthesis above, and the reaction was gently mixed and incubated at 16° C. for 16 hours: distilled water (25 $\mu$l); 5×T4 DNA ligase buffer (10 $\mu$l); Sal I adapters (10 $\mu$l); T4 DNA ligase (5 $\mu$l). The final composition of the reaction was the following: 50 mM Tris-HCl (pH 7.6); 10 mM MgCl$_2$; 1 mM ATP; 5% (w/v) PEG 8000; 1 mM DTT; 200 $\mu$g/ml Sal 1 adapters; 100 U/ml T4 DNA ligase. The reaction was extracted through phenol:chloroform:isoamyl alcohol (25:24:1, 50 $\mu$l), the aqueous phase removed, collected and diluted into 5M NaCl (8 $\mu$l) and absolute ethanol (−20° C., 250 $\mu$l). This was then centrifuged for 20 minutes at 14,000×g, the supernatant removed and the pellet was resuspended in 0.5 ml 70% ethanol, and centrifuged again for 2 minutes at 14,000×g. Subsequently, the supernatant was removed and the resulting pellet dried in a speedvac and carried on into the next procedure.

Enzymatic Digestion

To the cDNA prepared with the Sal 1 adapter from the previous paragraph was added the following reagents and the mixture was incubated at 37° C. for 2 hours: DEPC-treated water (41 $\mu$l); Not 1 restriction buffer (REACT, Life Tech., 5 $\mu$l), Not 1 (4 $\mu$l). The final composition of this reaction was the following: 50 mM Tris-HCl (pH 8.0); 10 mM MgCl$_2$; 100 mM MaCl; 1,200 U/ml Not 1.

Gel Isolation of cDNA

The cDNA is size fractionated by acrylamide gel electrophoresis on a 5% acrylamide gel, and any fragments which were larger than 1 Kb, as determined by comparison with a molecular weight marker, were excised from the gel. The cDNA was then electroeluted from the gel into 0.1×TBE buffer (200 µl) and extracted with phenol:chloroform:isoamyl alcohol (25:24:1, 200 µl). The aqueous phase was removed, collected and centrifuged for 20 minutes at 14,000×g. The supernatant was removed from the DNA pellet which was resuspended in 70% ethanol (0.5 ml) and centrifuged again for 2 minutes at 14,000×g. The supernatant was again discarded, the pellet dried in a speedvac and resuspended in distilled water (15 µl).

Ligation of cDNA into pRK5 Vector

The following reagents were added together and incubated at 16° C. for 16 hours: 5×T4 ligase buffer (3 µl); pRK5, Xho1, Not1 digested vector, 0.5 µg, 1 µl); cDNA prepared from previous paragraph (5 µl) and distilled water (6 µl). Subsequently, additional distilled water (70 µl) and 10 mg/ml tRNA (0.1 µl) were added and the entire reaction was extracted through phenol:chloroform:isoamyl alcohol (25:24:1). The aqueous phase was removed, collected and diluted into 5M NaCl (10 µl) and absolute ethanol (−20° C., 250 µl). This was then centrifuged for 20 minutes at 14,000× g, decanted, and the pellet resuspended into 70% ethanol (0.5 ml) and centrifuged again for 2 minutes at 14,000×g. The DNA pellet was then dried in a speedvac and eluted into distilled water (3 µl) for use in the subsequent procedure.

Transformation of Library Ligation into Bacteria

The ligated cDNA/pRK5 vector DNA prepared previously was chilled on ice to which was added electrocompetent DH10B bacteria (Life Tech., 20 µl). The bacteria vector mixture was then electroporated as per the manufacturers recommendation. Subsequently SOC media (1 ml) was added and the mixture was incubated at 37° C. for 30 minutes. The transformants were then plated onto 20 standard 150 mm LB plates containing ampicillin and incubated for 16 hours (370° C.) to allow the colonies to grow. Positive colonies were then scraped off and the DNA isolated from the bacterial pellet using standard CsCl-gradient protocols. For example, Ausubel et al., 2.3.1.

Identification of FLS 139

FLS139 can be identified in the human fetal liver library by any standard method known in the art, including the methods reported by Klein R. D. et al. (1996), *Proc. Natl. Acad. Sci.* 93, 7108–7113 and Jacobs (U.S. Pat. No. 5,563, 637 issued Jul. 16, 1996). According to Klein et al. and Jacobs, cDNAs encoding novel secreted and membrane-bound mammalian proteins are identified by detecting their secretory leader sequences using the yeast invertase gene as a reporter system. The enzyme invertase catalyzes the breakdown of sucrose to glucose and fructose as well as the breakdown of raffinose to sucrose and melibiose. The secreted form of invertase is required for the utilization of sucrose by yeast (*Saccharomyces cerevisiae*) so that yeast cells that are unable to produce secreted invertase grow poorly on media containing sucrose as the sole carbon and energy source. Both Klein R. D., supra, and Jacobs, supra, take advantage of the known ability of mammalian signal sequences to functionally replace the native signal sequence of yeast invertase. A mammalian cDNA library is ligated to a DNA encoding a nonsecreted yeast invertase, the ligated DNA is isolated and transformed into yeast cells that do not contain an invertase gene. Recombinants containing the nonsecreted yeast invertase gene ligated to a mammalian signal sequence are identified based upon their ability to grow on a medium containing only sucrose or only raffinose as the carbon source. The mammalian signal sequences identified are then used to screen a second, full-length cDNA library to isolate the full-length clones encoding the corresponding secreted proteins.

The nucleotide sequence of FLS139 in shown in FIGS. 1A-1 and 1A-2 (SEQ ID. NO: 16), while its amino acid sequence is shown in FIGS. 1B-1 and 1B-2 (SEQ ID NO: 17). FLS139 contains a fibrinogen-like domain exhibiting a high degree of sequence homology with the two known human ligands of the TIE-2 receptor (h-TIE2L1 and h-TIE2L2). Accordingly, FLS139 has been identified as a novel member of the TIE ligand family.

A clone of FLS139 and deposited with the American Type Culture Collection (ATCC), 1081 University Boulevard, Manassa, Va. 20110-2209, on Sep. 18, 1997 under the terms of the Budapest Treaty, and has been assigned the deposit number ATCC209281.

EXAMPLE 1

Identification of NL1

NL1 was identified by screening the GenBank database using the computer program BLAST (Altshul et al., *Methods in Enzymology* 266:460–480 (1996). The NL1 sequence shows homology with known expressed sequence tag (EST) sequences T35448, T11442, and W77823. None of the known EST sequences have been identified as full length sequences, or described as ligands associated with the TIE receptors.

Following its identification, NL1 was cloned from a human fetal lung library prepared from mRNA purchased from Clontech, Inc. (Palo Alto, Calif., USA), catalog # 6528-1, following the manufacturer's instructions. The library was screened by hybridization with synthetic oligonucleotide probes:

NL1.5-1
  5'-GCTGACGAACCAAGGCAACTACAAACTCCTG-GT SEQ. ID. NO: 7
NL1.3-1
  5'-TGCGGCCGGACCAGTCCTCCATGGTCACCAG-GAGTTTGTAG SEQ. ID. NO: 8
NL1.3-2
  5'-GGTGGTGAACTGCTTGCCGTTGTGCCATGTAAA SEQ. ID. NO: 9 based on the ESTs found in the GenBank database. cDNA sequences were sequenced in their entireties.

The nucleotide and amino acid sequences of NL1 are shown in FIGS. 2A and 2B (SEQ ID NO: 1) and FIGS. 3A and 3B (SEQ ID NO: 2), respectively.

NL1 shows a 23% sequence identity with both the TIE1 and the TIE2 ligand.

A clone of NL1 and deposited with the American Type Culture Collection (ATCC), 1081 University Boulevard, Manassa, Va. 20110-2209, on Sep. 18, 1997 under the terms of the Budapest Treaty, and has been assigned the deposit number ATCC20928.

EXAMPLE 2

Identification of NL5 and NL8

An expressed sequence tag (EST) DNA database (LIFESEQ™, Incyte Pharmaceuticals, Palo Alto, Calif.) was searched and ESTs were identified that showed homology to the FLS139 protein of Reference Example 1. To clone NL5 and NL8, a human fetal lung library prepared from mRNA purchased from Clontech, Inc. (Palo Alto, Calif., USA), catalog # 6528-1 was used, following the manufacturer's instructions. The library was screened by hybridization with synthetic oligonucleotide probes:
NL5
NL5.5-1 5'CAGGTTATCCCAGAGATTTAATGCCACCA SEQ. ID. NO: 10

NL5.3-1 5'TTGGTGGGAGAAGTTGCCAGATCAGGTG-GTGGCA SEQ. ID. NO: 11
NL5.3-2 5'TTCACACCATAACTGCATTGGTCCA SEQ. ID. NO: 12
NL8
NL8.5-1 5'ACGTAGTTCCAGTATGGTGTGAGCAG-CAACTGGA SEQ. ID. NO: 13
NL8.3-1 5'AGTCCAGCCTCCACCCTCCAGTTGCT SEQ. ID. NO: 14
NL8.3-2 5'CCCCAGTCCTCCAGGAGAACCAGCA SEQ. ID. NO: 15
based on the ESTs found in the database. cDNA sequences were sequenced in their entireties. cDNA clones were sequenced. The entire nucleotide and deduced amino acid sequences of NL5 are shown in FIGS. 4A–4C and 5A and 5B (SEQ ID Nos: 3 and 4). The entire nucleotide and deduced amino acid sequences of NL8 are shown in FIGS. 6A and 6B and 7A and 7B (SEQ. ID. Nos: 5 and 6).

Based on a BLAST and FastA sequence alignment analysis (using the ALIGN program) of the full-length sequences, NL5 shows a 24% sequence identity with both ligand 1 and ligand 2 of the TIE2 receptor. NL8 shows a 23% sequence identity with both ligand 1 and ligand 2 of the TIE2 receptor.

The fibrinogen domains of the TIE ligand homologues NL1, NL5 and NL8 are 64–74% identical. More specifically, the fibrinogen domain of NL1 is 74% identical with the fibrinogen domain of NL5 and 63% identical with the fibrinogen domain of NL8, while the fibrinogen domain of NL5 is 57% identical with the fibrinogen domain of NL8. Ligand 1 and ligand 2 of the TIE-2 receptor are 64% identical and 40–43% identical to NL1, NL5 and NL8.

EXAMPLE 3
Northern Blot and in situ RNA Hybridization Analysis

Expression of the NL1 and NL5 mRNA in human tissues was examined by Northern blot analysis. Human mRNA blots were hybridized to a $^{32}$P-labeled DNA probe based on the full length cDNAs; the probes were generated by digesting and purifying the cDNA inserts. Human fetal RNA blot MTN (Clontech) and human adult RNA blot MTN-II (Clontech) were incubated with the DNA probes. Blots were incubated with the probes in hybridization buffer (5×SSPE; 2Denhardt's solution; 100 mg/nL denatured sheared salmon sperm DNA; 50% formamide; 2% SDS) for 60 hours at 42° C. The blots were washed several times in 2×SSC; 0.05% SDS for 1 hour at room temperature, followed by a 30 minute wash in 0.1×SSC; 0.1% SDS at 50° C. The blots were developed after overnight exposure by phosphorimager analysis (Fuji).

Figure 11:
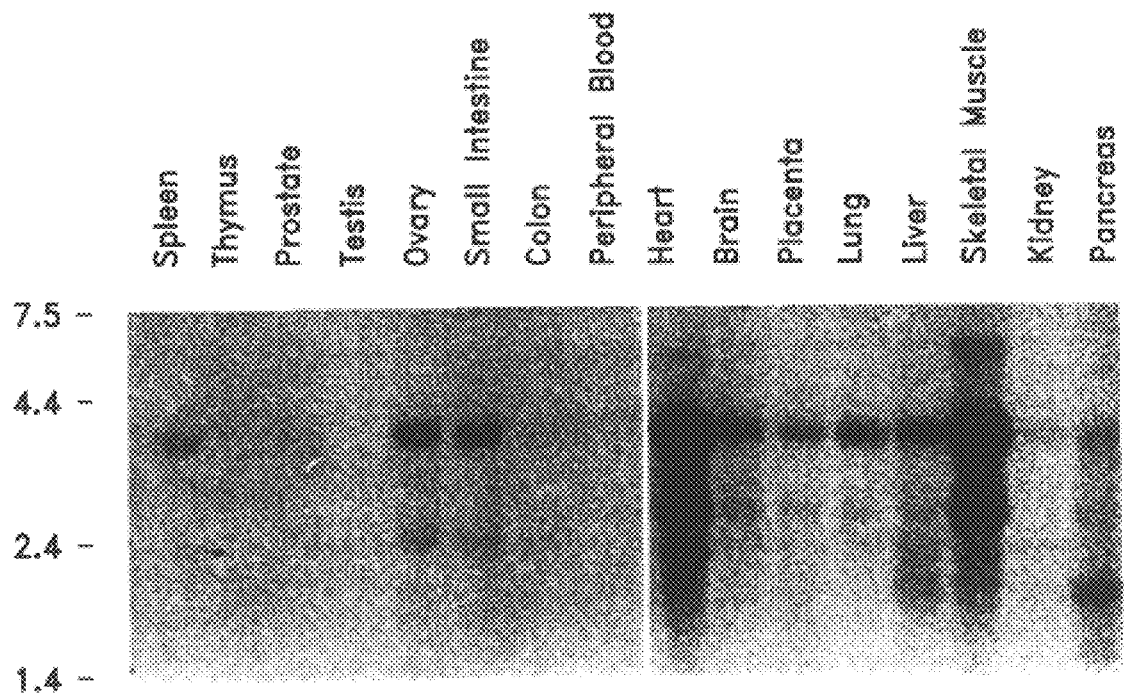
FIGS. 11 and 12—Northern blots showing the expression of the mRNAs of TIE ligand homologues NL1 and NL5 in various tissues.
Figure 12:
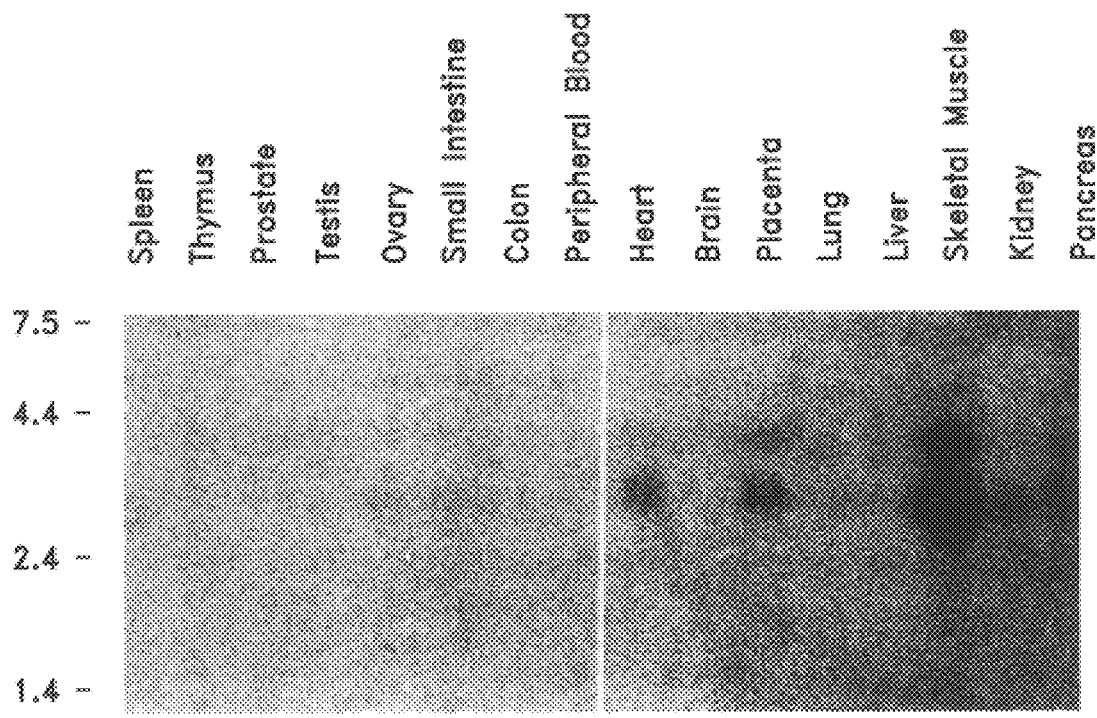

As shown in FIGS. 11 and 12, NL1 and NL5 mRNA transcripts were detected. Strong NL1 mRNA expression was detected in heart and skeletal muscle tissue and in the pancreas. NL5 mRNA was strongly expressed in skeletal muscle, and, to a lesser degree, heart, placenta and pancreas.

Figure 8B:
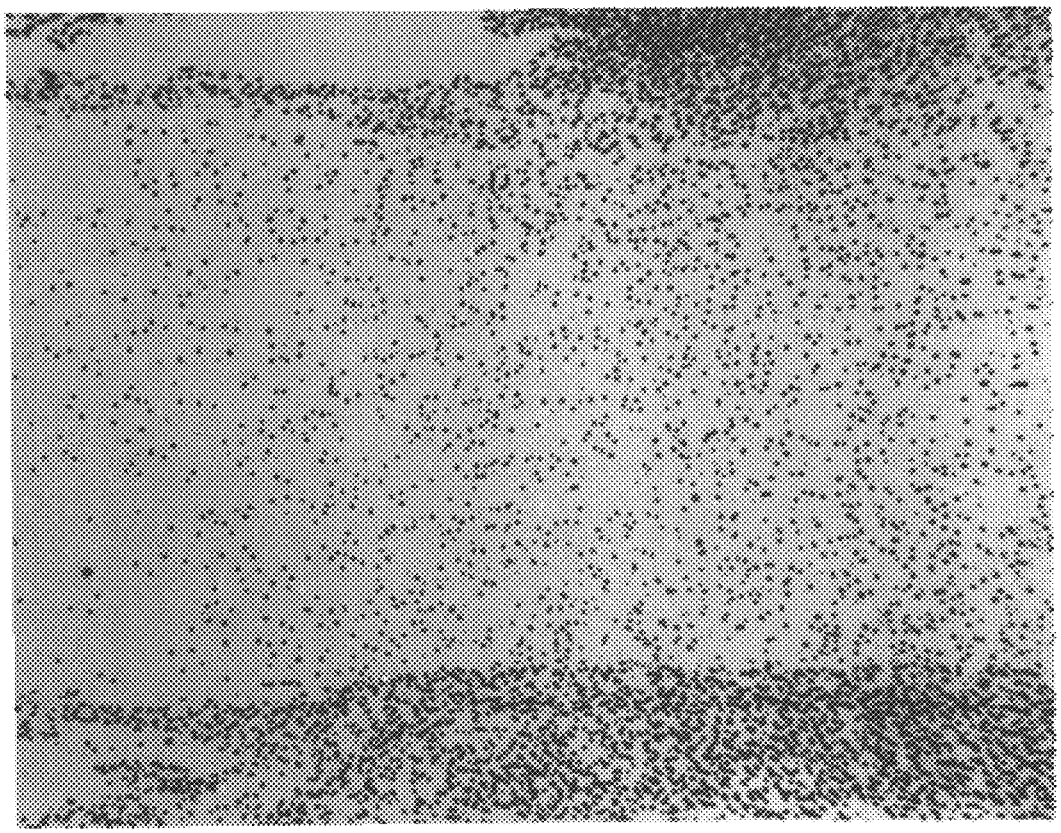

In situ hybridization results show that NL1 is expressed in the cartilage of developing long bones and in periosteum adjacent to differentiating osteoblasts. Expression was also observed in connective tissue at sites of synovial joint formation, in connective tissue septa, and in the periosteum of fetal body wall (FIGS. 8A and 8B).

In situ hybridization was performed using an optimized protocol, using PCR-generated $^{33}$P-labeled riboprobes. (Lu and Gillett, Cell Vision 1: 169–176 (1994)). Formalin-fixed, paraffin-embedded human fetal and adult tissues were sectioned, deparaffinized, deproteinated in proteinase K (20 g/ml) for 15 minutes at 37° C., and further processed for in situ hybridization as described by Lu and Gillett (1994). A [$^{33}$-P] UTP-labeled antisense riboprobe was generated from a PCR product and hybridized at 55° C. overnight. The slides were dipped in Kodak NTB2 nuclear track emulsion and exposed for 4 weeks.

Figure 9A:
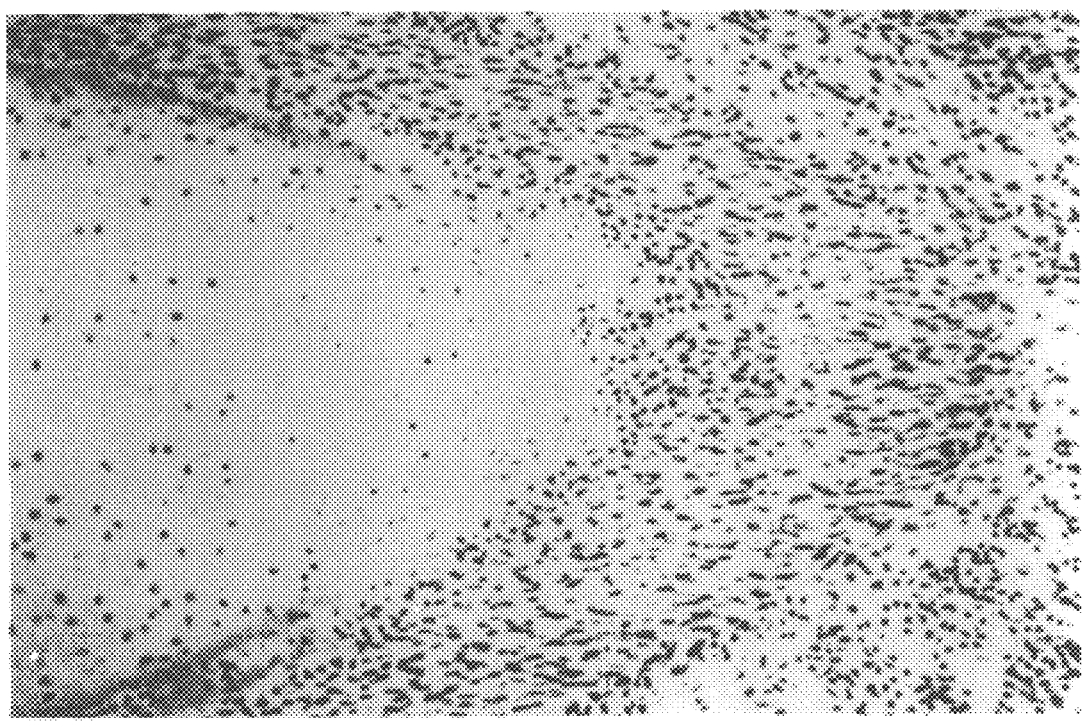
FIGS. 9A and 9B show the expression of NL5 in various tissues as determined by in situ hybridization to cellular RNA.
Figure 9B:
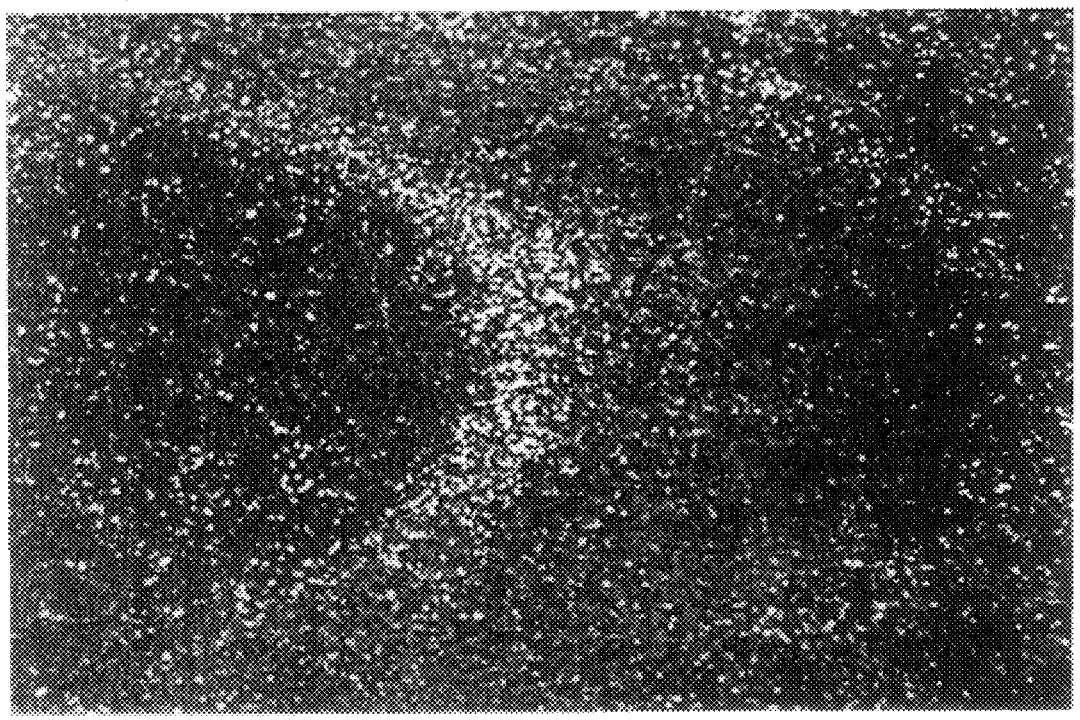

In situ hybridization indicated NL5 mRNA expression in adult human breast cancel cells over benign breast epithelium, areas of apocrine metaplasia and sclerosing adenosis. Expression was further observed over infiltrating breast ductal carcinoma cells. In fetal lower limb tissue, high expression was found at sites of enchondral bone formation, in osteocytes and in periosteum/perichondrium of developing bones. NL5 mRNA was also highly expressed in osteocytes and in periosteum/periochondrium of developing bones of fetal body wall tissue. This distribution suggests a role in bone formation and differentiation (FIGS. 9A and 9B).

Figure 10A:
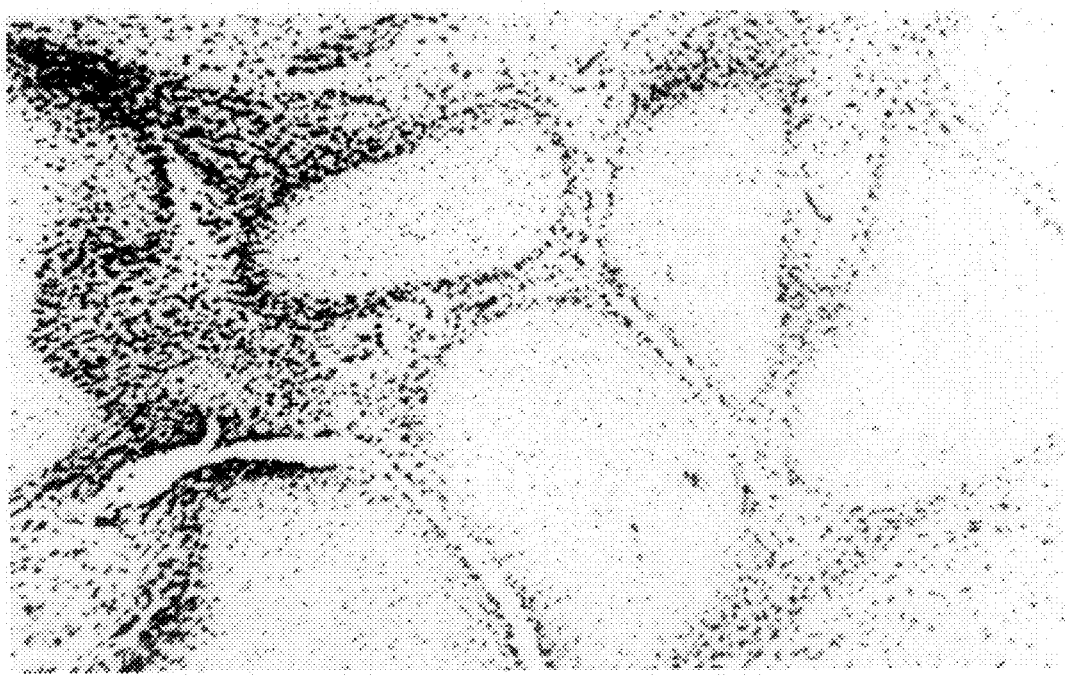
FIGS. 10A and 10B show the expression of NL8 in various tissues as determined by in situ hyridization to cellular RNA.
Figure 10B:
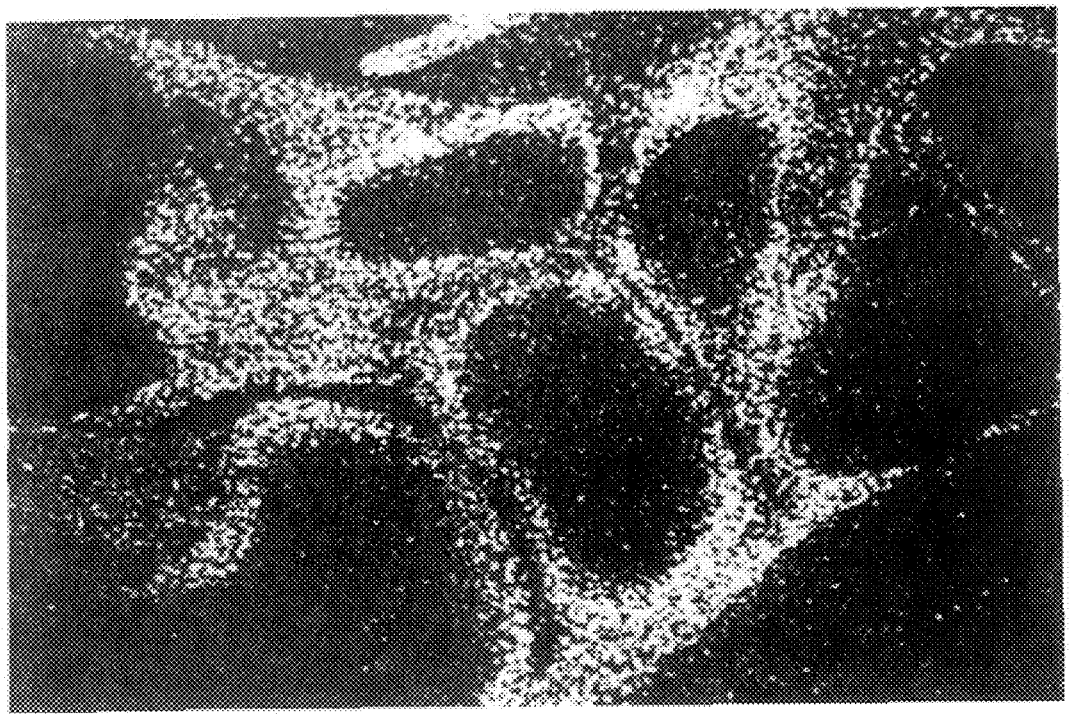

In situ hybridization for NL8 showed highly organized expression pattern in the developing limb, intestine and body wall, suggesting a distinctive functional role at this site, and potential involvement in angiogenesis and patterning (FIGS. 10A and 10B). This expression pattern is distinct from that of NL1 and NL5.

EXAMPLE 4
Expression of NL1, NL5, and NL8 in E. coli

This example illustrates the preparation of an unglycosylated form of the TIE ligand homologues of the present invention in E. coli. The DNA sequence encoding a NL1, NL5 or NL8 ligand (SEQ. ID. NOs: 1, 3, and 5, respectively) is initially amplified using selected PCR primers. The primers should contain restriction enzyme sites which correspond to the restriction enzyme sites on the selected expression vector. A variety of expression vectors may be employed. The vector will preferably encode an antibiotic resistance gene, an origin of replication, e promoter, and a ribozyme binding site. An example of a suitable vector is pBR322 (derived from E. coli; see Bolivar et al., Gene 2:95 (1977)) which contains genes for ampicillin and tetracycline resistance. The vector is digested with restriction enzyme and dephosphorylated. The PCR amplified sequences are then ligated into the vector.

The ligation mixture is then used to transform a selected E. coli strain, using the methods described in Sambrook et al., supra. Transformants are identified by their ability to grow on LB plates and antibiotic resistant colonies are then selected. Plasmid DNA can be isolated and confirmed by restriction analysis.

Selected clones can be grown overnight in liquid culture medium such as lB broth supplemented with antibiotics. The overnight culture may subsequently be used to inoculate a later scale culture. The cells are then grown to a desired optical density. An inducer, such as IPTG may be added.

After culturing the cells for several more hours, the cells can be harvested by centrifugation. The cell pellet obtained by the centrifugation can be solubilized using various agents known in the art, and the solubilized protein can then be purified using a metal chelating column under conditions that allow tight binding of the protein.

EXAMPLE 5
Expression of NL1, NL5 and NL8 in Mammalian Cells

This example illustrates preparation of a glycosylated form of the NL1, NL5 and NL8 ligands by recombinant expression in mammalian cells.

The vector, pRK5 (see EP 307,247, published Mar. 15, 1989), is employed as the expression vector. Optionally, the NL1, NL5 and NL8 DNA is ligated into pRK5 with selected restriction enzymes to allow insertion of the NL1, NL5 and NL8 DNA using ligation methods such as described in Sambrook et al., supra. The resulting vector is called pRK5-NL1, NL5 and NL8, respectively.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-NL1, NL5 and NL8 DNA is mixed with about 1 μg DNA encoding the VA RNA gene [Thimmappaya et al., Cell, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of NL1, NL5 and NL8 polypeptide. The cultures containing transfected cells may undergo further incubation (in serum free medium) and the medium is tested in selected bioassays.

In an alternative technique, NL1, NL5 and NL8 may be introduced into 293 cells transiently using the dextran sulfate method described by Somparyrac et al., Proc. Natl. Acad. Sci., 12:7575 (1981). 293 cells are grown to maximal density in a spinner flask and 700 μg pRK5-NL1, NL5 and NL8 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and reintroduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed NL1, NL5 and NL8 can then be concentrated and purified by any selected method, such as dialysis and/or column chromatography.

In another embodiment, NL1, NL5 and NL8 can be expressed in CHO cells. The pRK5-NL1, NL5 and NL8 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of NL1, NL5 and NL8 polypeptide, the culture medium may be replaced with serum free medium. Preferably, the cultures are incubated for about 6 days, and then the conditioned medium is harvested. The medium containing the expressed NL1, NL5 and NL8 can then be concentrated and purified by any selected method.

Epitope-tagged NL1, NL5 and NL8 may also be expressed in host CHO cells. NL1, NL5 and NL8 may be subcloned out of the pRK5 vector. The subclone insert can undergo PCR to fuse in frame with a selected epitope tag such as a poly-his tag into a Baculovirus expression vector. The poly-his tagged NL1, NL5 and NL8 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged NL1, NL5 and NL8 can then be concentrated and purified by any selected method, such as by $Ni^{2+}$-chelate affinity chromatography.

EXAMPLE 6

Expression of NL1, NL5 and NL8 in Yeast

First, yeast expression vectors are constructed for intracellular production or secretion of NL1, NL5 and NL8 from the ADH2/GAPDH promoter. DNA encoding NL1, NL5 and NL8, a selected signal peptide and the promoter is inserted into suitable restriction enzyme sites in the selected plasmid to direct intracellular expression of NL1, NL5 and NL8. For secretion, DNA encoding NL1, NL5 and NL8 can be cloned into the selected plasmid, together with DNA encoding the ADH2/GAPDH promoter, the yeast alpha-factor secretory signal/leader sequence, and linker sequences (if needed) for expression of NL1, NL5 and NL8.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant NL1, NL5 and NL8 can subsequently be isolated and purified by removing the yeast cells from the fermentation medium by centrifugation and then concentrating the medium using selected cartridge filters. The concentrate containing NL1, NL5 and NL8 may further be purified using selected column chromatography resins.

EXAMPLE 7

Expression of NL1, NL2 and NL8 in Baculovirus

The following method describes recombinant expression of NL1, NL5 and NL8 in Baculovirus.

The NL1, NL5 and NL8 is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the NL1, NL5 and NL8 or the desired portion of the NL1, NL5 and NL8 (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged NL1, NL5 and NL8 can then be purified, for example, by $Ni^{2+}$-chelate affinity chromatography as follows. Extracts are prepared from recombinant virus-infected Sf9 cells as described by Rupert et al., *Nature*, 362:175–179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto, the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged NL1, NL5 and NL8 are pooled and dialyzed against loading buffer.

Alternatively, purification of the IgG tagged (or Fc tagged) NL1, NL5 and NL8 can be performed using known chromatography techniques, including for instance, Protein A or protein G column chromatography.

EXAMPLE 8
Preparation of Antibodies that Bind NL1, NL2 and NL8

This example illustrates preparation of monoclonal antibodies which can specifically bind NL1, NL2 and NL8.

Techniques for producing the monoclonal antibodies are known in the art and are described, for example, in Goding, supra. Immunogens that may be employed include purified ligands of the present invention, fusion proteins containing such ligands, and cells expressing recombinant ligands on the cell surface. Selection of the immunogen can be made by the skilled artisan without undue experimentation.

Mice, such as Balb/c, are immunized with the immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind food pads. The immunized mice are then boosted 10 to 12 days later with additional immunogen emulsified in the selected adjuvant. Thereafter, for several weeks, the mice might also be boosted with additional immunization injections. Serum samples may be periodically obtained from the mice by retro-orbital bleeding for testing ELISA assays to detect the antibodies.

After a suitable antibody titer has been detected, the animals "positive" for antibodies can be injected with a final intravenous injection of the given ligand. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the antigen. Determination of "positive" hybridoma cells secreting the desired monoclonal antibodies against the TIE ligand homologues herein is well within the skill in the art.

The positive hybridoma cells can be injected intraperitoneal into syngeneic Balb/c mice to produce ascites containing the anti-TIE-ligand homologue monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Deposit of Material

As noted before, the following materials have been deposited with the American Type Culture Collection, 10801 University Boulevard, Manassa, Va. 20110-2209, USA (ATCC).

| Material | ATCC Dep. No. | Deposit Date |
|---|---|---|
| NL1-DNA 22779-1130 | ATCC209280 | September 18, 1997 |
| NL5-DNA 28497-1130 | ATCC209279 | September 18, 1997 |
| NL8-DNA 23339-1130 | ATCC209282 | September 18, 1997 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of the deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and Commissioner's rules pursuant thereto (including 37 C.F.R. §1.14 with particular reference to 886 OG 683).

The assignee of the present application has agreed that if a culture of the materials on deposit should die ot be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The present specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of the invention. The deposit of material herein does not constitute an admission that the written description is inadequate to enable the practice of any aspect of the invention, including the best more thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated nucleic acid molecule encoding a polypeptide comprising an amino acid sequence having at least 90% sequence identity with the amino acid sequence of SEQ ID NO: 2, wherein said polypeptide is capable of inducing vascularization.

2. The isolated nucleic acid molecule of claim 1 which comprises the coding region of SEQ ID NO: 1.

3. The isolated nucleic acid molecule of claim 1 which comprises a nucleotide sequence encoding the fibrinogen-like domain of SEQ ID NO: 2.

4. The isolated nucleic acid molecule of claim 1 encoding a polypeptide comprising the amino acid sequence of SEQ ID NO: 2.

5. A vector which comprises the nucleic acid molecule of claim 1.

6. A recombinant host cell transformed with the nucleic acid molecule according to claim 1.

7. The recombinant host cell of claim 6 which is a prokaryotic cell.

8. The recombinant host cell of claim 6 which is a eukaryotic cell.

9. A vector which comprises the nucleic acid molecule of claim 2.

10. A vector which comprises the nucleic acid molecule of claim 3.

11. A vector which comprises the nucleic acid molecule of claim 4.

12. A recombinant host cell transformed with the nucleic acid molecule of claim 2.

13. A recombinant host cell transformed with the nucleic acid molecule of claim 3.

14. A recombinant host cell transformed with the nucleic acid molecule of claim 4.

* * * * *